(12) United States Patent
Coupland et al.

(10) Patent No.: US 6,265,637 B1
(45) Date of Patent: Jul. 24, 2001

(54) GENETIC CONTROL OF FLOWERING

(75) Inventors: George M. Coupland; Robert J. Schaffer, both of Norwich (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 09/202,712

(22) PCT Filed: Jun. 23, 1997

(86) PCT No.: PCT/GB97/01676

§ 371 Date: Jan. 11, 1999

§ 102(e) Date: Jan. 11, 1999

(87) PCT Pub. No.: WO97/49811

PCT Pub. Date: Dec. 31, 1997

(30) Foreign Application Priority Data

Jun. 21, 1996 (GB) .................................................. 9613132

(51) Int. Cl.[7] .............................. C12N 5/04; C12N 15/29; C12N 15/82; A01H 1/00; A01H 5/00
(52) U.S. Cl. ......................... 800/290; 435/69.1; 435/419; 435/468; 435/471; 435/320.1; 536/23.6; 800/266; 800/298
(58) Field of Search ................................ 435/69.1, 320.1, 435/410, 419, 468, 471; 536/23.6; 800/278, 290, 295, 298, 260, 266

(56) References Cited

FOREIGN PATENT DOCUMENTS 96 14414 5/1996 (WO) .

OTHER PUBLICATIONS

Schaffer et al, Cell, vol. 93, pp. 1219–1229, 1998.*
Simon R. and Coupland G.: "Arabidopsis genes that regulate flowering time in response to day–length" Seminars in Cell 7 Development Biology, vol. 7, No. 3, Jun. 1996, pp. 419–425, XP002044794 see whole document, esp. p. 422.

Zagotta M et al.: "Early–flowering mutants of *Arabidopsis thaliana*" Australian Journal of Plant Physiology, vol. 19, 1992, pp. 411–418, XP002044795 see whole document, esp. p. 416.
Jackson D. et al. : "Expression pattern of myb genes from Antirrhinum flowers" The Plant Cell, vol. 115–125, XP002044796 see whole document.
Baranoski N. et al.: A novel DNA binding protein with homology to myb oncorpoteins containing only one repeat can function as transcriptional activator The EMBO Journal, vo. 13, No. 22, Nov. 15, 1994 pp. 5383–5392, XP002044797 cited in the application.
Millar A. et al: "A novel circadian phenotype based on firefly luciferase expression in transgenic plants" The Plant Cell, vol. 4, No. 9, Sep. 1992, pp. 1075–1087, XP002044798 see whole document.
Martinez–Zapater J. et al.: "The transition to flowering in Arabidopsis; in Arabidopsis', pp. 403–433" 1994, Cold Spring Laboratory Press New York XP002044801 see whole document, esp. pp. 416–428.
Newman T. et al.: Genes galor: a summary of methods for accessing results from large–scale partial sequencing of anonymous Arabidopsis cDNA clones, AC R30439 EMBL Database, Aug. 11, 1995, Heidelberg, XP002044799 cited in the application see whole document.
Coupland G. : "Regulation of flowering by photoperiod in Arabidopsis" Plant, Cell and Enviroment, vol. 20, 1997, pp. 785–789, XP002044800 see esp. 788/89.

* cited by examiner

*Primary Examiner*—Gary Benzion
*Assistant Examiner*—Ashwin Mehta
(74) *Attorney, Agent, or Firm*—Nixon & Vanderhye P.C.

(57) ABSTRACT

A flowering characteristic of a plant, particularly the timing of flowering, is controlled by the expression of the Late Elongated Hypocotyl (LHY) gene of *Arabidopsis thaliana* or a mutant, variant, allele, derivative, or homologue thereof. Over-expression may be used to delay flowering in a transgenic plant. The promoter of the gene regulates transcription in accordance with the circadian rhythm and may be used to control expression of genes whose products are only required or desired at certain times of the day.

15 Claims, 12 Drawing Sheets

Figure 1(a)

Figure 2:
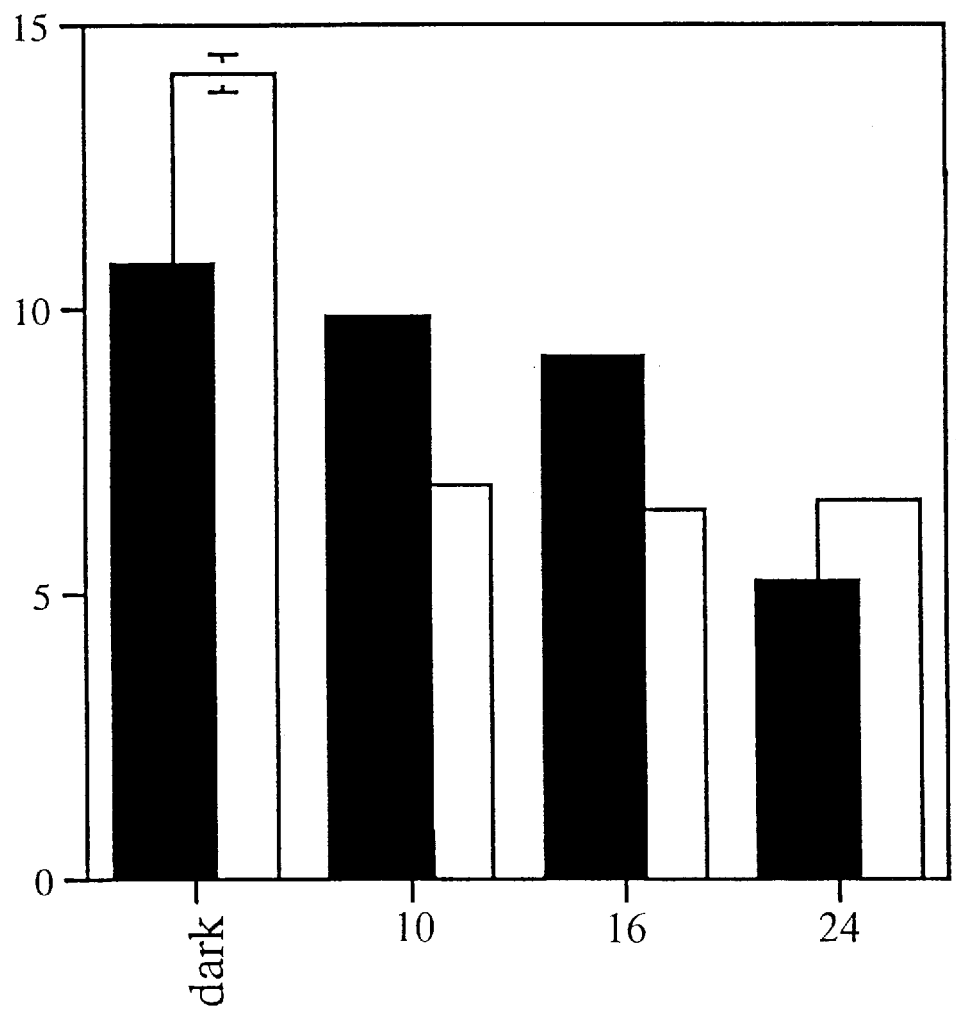

```
   1  CAGTTATCTTCTTCCTTCTTCTCTCTGTTTTTTAAATTTATTTTTAGAGAATTTTTTTTG    60
                         (Deleted in lhy)
  61  TTTTGCTTCCGATTTGATTATTTCCGGGAACGATGACTTCTCCGGGGAGTTCCCGGTGAG   120

121  ATGATAAGTCAGATTGCATACTTGTCTCCTCCATGGCTACTCTCAAGGGTTTTGGCTGCG   180
                              ▼ Position of the Ds.
 181  GTGGATTCGTTTGGTTTCTCTAGAATCTAAAGAGGTTATCACAACGGCTTTGCAATTTGA   240

241  AAACTTTCATGTTTGGGGAGATCAAAGATGGTTTCTTTTTTATACTTTACTTGTTAGAGA   300

301  GGATTTGAAGCAGCGAATAGCTGCAACCGGTCCTGTTATGGATACTAATACATCTGGAGA   360
                                                  M  D  T  N  T  S  G  E
 361  AGAATTATTAGCTAAGGCAAGAAAGCCATATACAATAACAAAGCAGCGAGAGCGATGGAC   420
       E  L  L  A  K  A  R  K  P  Y  T  I  T  K  Q  R  E  R  W  T
 421  TGAGGATGAGCATGAGAGGTTTCTAGAAGCCTTGAGGCTTTATGGAAGAGCTTGGCAACG   480
       E  D  E  H  E  R  F  L  E  A  L  R  L  Y  G  R  A  W  Q  R
 481  AATTGAAGAACATATTGGGACAAAGACTGCTGTTCAGATCAGAAGTCATGCACAAAAGTT   540
       I  E  E  H  I  G  T  K  T  A  V  Q  I  R  S  H  A  Q  K  F
 541  CTTCACAAAGTTGGAGAAAGAGGCTGAAGTTAAAGGCATCCCTGTTTGCCAAGCTTTGGA   600
       F  T  K  L  E  K  E  A  E  V  K  G  I  P  V  C  Q  A  L  D
 601  CATAGAAATTCCGCCTCCTCGTCCTAAACGAAAACCCAATACTCCTTATCCTCGAAAACC   660
       I  E  I  P  P  P  R  P  K  R  K  P  N  T  P  Y  P  R  K  P
 661  TGGGAACAACGGTACATCTTCCTCTCAAGTATCATCAGCAAAAGATGCAAAACTTGTTTC   720
       G  N  N  G  T  S  S  S  Q  V  S  S  A  K  D  A  K  L  V  S
 721  ATCGGCCTCTTCTTCACAGTTGAATCAGGCGTTCTTGGATTTGGAAAAAATGCCGTTCTC   780
       S  A  S  S  S  Q  L  N  Q  A  F  L  D  L  E  K  M  P  F  S
 781  TGAGAAAACATCAACTGGAAAAGAAAATCAAGATGAGAATTGCTCGGGTGTTTCTACTGT   840
       E  K  T  S  T  G  K  E  N  Q  D  E  N  C  S  G  V  S  T  V
 841  GAACAAGTATCCCTTACCAACGAAACAGGTAAGTGGCGACATTGAAACAAGTAAGACCTC   900
       N  K  Y  P  L  P  T  K  Q  V  S  G  D  I  E  T  S  K  T  S
 901  AACTGTGGACAACGCGGTTCAAGATGTTCCCAAGAAGAACAAAGACAAAGATGGTAACGA   960
       T  V  D  N  A  V  Q  D  V  P  K  K  N  K  D  K  D  G  N  D
 961  TGGTACTACTGTGCACAGCATGCAAAACTACCCTTGGCATTTCCACGCAGATATTGTGAA  1020
       G  T  T  V  H  S  M  Q  N  Y  P  W  H  F  H  A  D  I  V  N
1021  CGGGAATATAGCAAAATGCCCTCAAAATCATCCCTCAGGTATGGTATCTCAAGACTTCAT  1080
       G  N  I  A  K  C  P  Q  N  H  P  S  G  M  V  S  Q  D  F  M
1081  GTTTCATCCTATGAGAGAAGAAACTCACGGGCACGCAAATCTTCAAGCTACAACAGCATC  1140
       F  H  P  M  R  E  E  T  H  G  H  A  N  L  Q  A  T  T  A  S
1141  TGCTACTACTACAGCTTCTCATCAAGCGTTTCCAGCTTGTCATTCACAGGATGATTACCG  1200
       A  T  T  T  A  S  H  Q  A  F  P  A  C  H  S  Q  D  D  Y  R
1201  TTCGTTTCTCCAGATATCATCTACTTTCTCCAATCTTATTATGTCAACTCTCCTACAGAA  1260
       S  F  L  Q  I  S  S  T  F  S  N  L  I  M  S  T  L  L  Q  N
1261  TCCTGCAGCTCATGCTGCAGCTACATTCGCTGCTTCGGTCTGGCCTTATGCGAGTGTCGG  1320
       P  A  A  H  A  A  A  T  F  A  A  S  V  W  P  Y  A  S  V  G
1321  GAATTCTGGTGATTCATCAACCCCAATGAGCTCTTCTCCTCCAAGTATAACTGCCATTGC  1380
       N  S  G  D  S  S  T  P  M  S  S  P  P  S  I  T  A  I  A
1381  CGCTGCTACAGTAGCTGCTGCAACTGCTTGGTGGGCTTCTCATGGACTTCTTCCTGTATG  1440
       A  A  T  V  A  A  A  T  A  W  W  A  S  H  G  L  L  P  V  C
1441  CGCTCCAGCTCCAATAACATGTGTTCCATTCTCAACTGTTGCAGTTCCAACTCCAGCAAT  1500
       A  P  A  P  I  T  C  V  P  F  S  T  V  A  V  P  T  P  A  M
1501  GACTGAAATGGATACCGTTGAAAATACTCAACCGTTTGAGAAACAAAACACAGCTCTGCA  1560
       T  E  M  D  T  V  E  N  T  Q  P  F  E  K  Q  N  T  A  L  Q
1561  AGATCAAACCTTGGCTTCGAAATCTCCAGCTTCATCATCTGATGATTCAGATGAGACTGG  1620
       D  Q  T  L  A  S  K  S  P  A  S  S  S  D  D  S  D  E  T  G
```

Figure 1(b)

```
1621 AGTAACCAAGCTAAATGCCGACTCAAAAACCAATGATGATAAAATTGAGGAGGTTGTTGT  1680
      V  T  K  L  N  A  D  S  K  T  N  D  D  K  I  E  E  V  V  V
1681 TACTGCCGCTGTGCATGACTCAAACACTGCCCAGAAGAAAAATCTTGTGGACCGCTCATC  1740
      T  A  A  V  H  D  S  N  T  A  Q  K  K  N  L  V  D  R  S  S
1741 GTGTGGCTCAAATACACCTTCAGGGAGTGACGCAGAAACTGATGCATTAGATAAAATGGA  1800
      C  G  S  N  T  P  S  G  S  D  A  E  T  D  A  L  D  K  M  E
1801 GAAAGATAAAGAGGATGTGAAGGAGACAGATGAGAATCAGCCAGATGTTATTGAGTTAAA  1860
      K  D  K  E  D  V  K  E  T  D  E  N  Q  P  D  V  I  E  L  N
1861 TAACCGTAAGATTAAAATGAGAGACAACAACAGCAACAACAATGCAACTACTGATTCGTG  1920
      N  R  K  I  K  M  R  D  N  N  S  N  N  N  A  T  T  D  S  W
1921 GAAGGAAGTCTCCGAAGAGGGTCGTATAGCGTTTCAGGCTCTCTTTGCAAGAGAAAGATT  1980
      K  E  V  S  E  E  G  R  I  A  F  Q  A  L  F  A  R  E  R  L
1981 GCCTCAAAGCTTTTCGCCTCCTCAAGTGGCAGAGAATGTGAATAGAAAACAAAGTGACAC  2040
      P  Q  S  F  S  P  P  Q  V  A  E  N  V  N  R  K  Q  S  D  T
2041 GTCAATGCCATTGGCTCCTAATTTCAAAAGCCAGGATTCTTGTGCTGCAGACCAAGAAGG  2100
      S  M  P  L  A  P  N  F  K  S  Q  D  S  C  A  A  D  Q  E  G
2101 AGTAGTAATGATCGGTGTTGGAACATGCAAGAGTCTTAAAACGAGACAGACAGGATTTAA  2160
      V  V  M  I  G  V  G  T  C  K  S  L  K  T  R  Q  T  G  F  K
2161 GCCATACAAGAGATGTTCAATGGAAGTGAAAGAGAGCCAAGTTGGGAACATAAACAATCA  2220
      P  Y  K  R  C  S  M  E  V  K  E  S  Q  V  G  N  I  N  N  Q
2221 AAGTGATGAAAAAGTCTGCAAAAGGCTTCGATTGGAAGGAGAAGCTTCTACATGACAGAC  2280
      S  D  E  K  V  C  K  R  L  R  L  E  G  E  A  S  T
2281 TTGGAGGTAAAAAAAAAACATCCACATTTTTATCAATATCTTTAAATCTAGTGTTAGTAG  2340

2341 TTTGCTTCTCCAATCTTTATGAAAGAGACTTTTAATTTTCCTTCCGAACATTTCTTTGGT  2400

2401 CATGTCAGGTTCTGTACCATATTACCCCATGTCTTGTCTCTTGTCTCTGTTTGTGTATGC  2460

2461 TACTTGTGGTCTATATGTCATCTGCTACTACTGTTAATTAACCATTAAGCAATGGATTTG  2520

2521 TCTTTA  2526
```

Figure 3

A.

```
  1  CGTTACCGAC CGTTTTCATC CCTATACTCA AAAGAGTAAC CAGTACGTTT
              D71
 51  GATTCGTCTT GATGGAACTC AAAGCTAAGT ATTTTCAAAT TACATTGTGG
101  ATGATCCAGA TGTGAGCAAG TGATT
     Sau 3A        DL4
```

B.

```
  1  ATCCTACTTT CATCCCTGCT AAAGAGGTTA TCACAACGGC TTTGCAATTT
            D73
 51  GAAAACTTTC ATGTTTGGGG AGATCAAAGA TGGTTTCTTT TTTATACTTT
101  ACTTGTTAGA GAGGATTTGA AGCAGCGAAT AGCTGCACCG GTCCTGTTAT
151  GGATACTAAT ACATCTGGAG AAGAATTATT AGCTAAGGTA CTACTACTAA
201  TGAAATAAGA TTGGTGTTTT TTTGTTTGAG AGATTTGGAC TGTTGTTGTG
251  TGAAGATTTG ATTTTCTTTT GGGTTTTCAA ATGTTTAGGC AAGAAAGCCA
301  TATACAATAA CAAAGCAGCG AGRGCGATGG ACTGAGGATG AGCATGAGAG
351  GTTTCTAGAA GCCTTGAGGC TTTATGGAAG AGCTTGGCAA CGAATTGAAG
401  GTCGRAAGGT TTATCTTTTG AATGTTTAGT TTGAACTCTT TGAGATTTTA
451  TATTCCTTTG TTTAGGAGTG TCTTTATCTC CTCTTGATTG GGAGATTCCT
501  TCTTTTCTTT TCATTTGTG TGCAGAACAT ATTGGGACAA AGACTGCTGT
551  TCAGATCAGA AGTCATGCAC AAAAGTTCTT CACAAAGGTA AGTTGATGAT
601  CCTTTCAGAT CCCGGTGAAA CGGTCGGGAA ACTAGCTCTA CCGTTTCCGT
           Bst Y1                                       E4
651  TTCCGTTTAC CGTTTT
```

A. Wild type DNA

B. *lhy* DNA

Figure 6(a)

```
LHY   - TITKQRERWTEDEHERFLEALRLYGRAWQRIEEHIGTKTAVQIRSHAQKFFTKLE
                | |   | |||||||
TEC1  -         WSEKVEEAFLEALRLI
                |     |  |||
TEF1  -         WSPDIEQSFQEALAIY
                  α helix of TEA domain
```

Figure 6(b)

```
LHY   - TITKQRERWTEDEHERFLEALRLYGRAWQRIEEHIGTKTAVQIRSHAQKFFTKLE
                |:  |  :  |  | |:  :|  |   | |  :|||:    :|:::|
YCS3  -         WsvrEsqlFpElLkefGsqWslIsEklGTKsttnvRnyyQr LHY   - TITKQRERWTEDEHERFLEALRLYGRAWQRIEEHIGTKTAVQIRSHAQKFFTKLE
                ||::|  |:  |:|     :|   |   |   |   :|   |
BAS1 R1-        WTqeEdEqlLkAyeehGphWlsIsmdIpgrTedQcakryievlgpgs
                ||  :|    :   ::   |  |::|    :   : ::   |:   :|   :
     R2-        WTleEdlnliskvkayGtkWrkIssemefrpsltcRnrwrKiitmvv
```

Figure 7

```
            myb α1           myb α2            myb α3 hhhHHHHHHHHH    hhHHHHHHHH         hhhHHHHHHHHH

.k..WT$eEd..#..##...G..$W..IA..L.gRtd.q#..rw...lnp$
         ||: |    |  ||    |   |  |   :   :|  ||    :
LHY - TITKQRERWTEDEHERFLEALRLYG RAWQRIEEHIGTKTAVQIRSHAQKFFTKLE
```

Figure 8

```
LHY       - TITKQRERWTEDEHERFLEALRLYGRAWQRIEEHIGTKTAVQIRSHAQKFFTKLEKA
predicted        HHHHHHHHHHHHHHHH HHHHHHHHH LLLL    HHHHHHHHHHH
Prob. H     0023689999999999999858999889774000125489999999999832
Prob. L     8875310000000000000141000000125998731100000000000167
```

Figure 9

```
Arabidopsis EST - IATTEAGEAPEKKVRKAYTITKSRESWTEGEHDKFLEALQLFDRDWKKIEDFFGSKTVIQIRSHAQKYFLKVQKNGTLAHIPT
                   :: | :::| |:    :|||:||    ||:|||||||  |:    ::|:||:|  ::|||||||| :::|||  ::
LHY           - MDTNTSGEELLAKARKPYTITKQRERWTEDEHERFLEALRLYGRAWQRIEEHIGTKTAVQIRSHAQKFFTKLEKEAEVKGIPV (644)
LHY         - GRIAFQALFARERLPQSFSPPQV--AENVNRKQSDTSMPLAPNFKSQDSC------AADQEGVVMIGVGTCK-SLKTRQTGFKPYKRCSMEVK
              |:|||:|||||||||||||||      :||:|||   :   ::    :::           :   ::   |   ::  :: |||||||||||:|:|
Rice EST    - FDALFSRERLPQSFSPPQVEGSKEISKEEEDEVTTVTVDLNKNAAIIDQELDTADEPRASFPNELSNLKLKSRRTGFKPYKRCSVEAK
           (1)

LHY         - ESQVGNINNQSDEKVCKRLRLEGEAST
              |:|| :: :::::   ||  |: |
RICE EST    - ENRVPASDEVGTKRI--RLESEDRHDLLSTWV
```

Figure 10(a)

```
   1 CAAACATCAACGTAGGGATCCGTGAAATATTTAAATCCGGTTTGTTTGGTTATTTTGGAA    60
  61 TAATTTCGGTTATTTCAATTAGATTCGGGTAGTTCAGTTCTTCGGTTAGTAACAAAAACT   120
 121 GGTCTATTGTTTTTTGGTTAACCTAGAACCGAACCGAACTAACCAAAGTTCTCGGTAACC   180
 181 TTTTGTAGTGGCTTCCTGACCGATGAGGCCGTCAACTTCAAAAAATATTGCAACTAAGCT   240
 241 CTGCTCCAAAATTAGAGTATCTATAACTATGTTAAACGCTTCTGCTTTAAGCAAAACACA   300
 301 GTTGTAAGCTGGAATCTAAAAAAATGAGTGTAATGATGTTTGCTGAATTCCATAAATAAA   360
 361 TACTACATGCTTCGGTTAAGACTTAAGAGTAATTAATGTTCCTTAATTTCTACAAATGTT   420
 421 ATATAAGCAAGTTGACCAAAGTTCTCGATGATAATTTGTTGAAATTTTGTATAGGCATTG   480
 481 CATGATATTATATGAAAGATGAAGATTTTTATACAGACGCAAGTTCCCCGAGCAGTCCA    540
 541 AGCTTGTCGGGTTTAATTCAACTATGTTAATACGCAAATTTATATAGAATAGGCGTAAAA   600
 601 GTGAGGCCCATACAATGTCTTATTACAAGCCCAGATCCAGCATAGCCAATACGTAGCAGT   660
 661 ACACCATCACAGCTGGCACCGTACCCACTTGTTTAGTCGTCCAAGTTTGTACCAATAATC   720
 721 GTTTACACGTAAGCAATTGTGGACCACCACACTCACTTTTACCTACGTGAGCTTCACATT   780
 781 GAAGCTTCTGGCTCGTAGAGAAGCAACTTGAGATATACCAAAAAGTGCAGTAGACAGCCA   840
 841 CTACAATATCACCACGTGTCGATCTGCGATGACTTCTGTTTTTCCATTTATACCCTTGGT   900
 901 GCTGTTCCAGCCTCAAATAACTTTTCAATTAAAATTTTTCCAAAAATTAGGGGCAAAAAT   960
 961 TGTTGTGGCTGAGATTGCTTCTGGCTTCTCTTCTTCTTCTTCCAGTCTTCTTCAGCCTAA  1020
1021 AACAGTCTTCCTTCTTCTTCTTCTTCTTCTTCTTTCAGTTATCTTCTTCCTTCTTCT     1080
1081 CTCTGTTTTTTAAATTTATTTTAGAGATTTTTTTTGTTTTGCTTCCGATTTGATTATT    1140
1141 TCCGGGAACGATGACTTCTCCGGGGAGTTCCCGGTGAGATGATAAGTCAGATTGCATACT  1200
1201 TGTCTCCTCCATGGCTACTCTCAAGGGTATAACAGTTTACATTATGAGCAGTTTCTAGGA  1260
```

Figure 10(b)

```
1261  TTCCTATAACATACTAAGATCTCTGTTTGGCTGCTGAGAAACTTATACAAGCGCATTAAC  1320

1321  TAAATCTTATTAGCTCTAAAAGTTAGCATAAATGATACGAATCTGGTGATTGATTACTGA  1380

1381  TATGAAGATTTGTGAAGGTTTTGGCTGAGGTGGATTCGTTTGGGTGAGGCTTTTGTGAAT  1440

1441  AATAATAAAGGGAATTCTTTTGAGTTCTGCTGGAGAAGCAGCGACTGTTTCACGGTGGTC  1500

1501  TTTGAAAAGATTTCTCTTTTGAATTTCGCTCATCACTCTTATCTTAGTGTTTGTGGATAA  1560

1561  ATATTTCTCATAAAGTACTTTCTCCTTTGCAGTTTCTCTAGAATCTAAAGAGGTTATCAC  1620

1621  AACGGCTTTGCAATTTGAAAACTTTCATGTTTGGGGAGATCAAAGATGGTTTCTTTTTTA  1680

1681  TACTTTACTTGTTAGAGAGGATTTGAAGCAGCGAATAGCTGCAACCGGTCCTGTTATGGA  1740

1741  TACTAATACA  1750
```

Figure 11

```
  1  GGAAGTCTCCGAAGAGGGTCGTATAGCGTTNAGGCTCTCTTTGCAAGAGAAAGATTGCC   60
 61  TCAAAGCTTTTNGCCTCCTCAAGTGGCAGAGAATGTNAATAGAAAACAAAGTGACACGTC  120
121  AATGCCATTGGCTCCTAATTTCAAAAGCCAGGATTCTTGTNCTGCAGACCAAGAAGGAGT  180
181  AGTAATNATCGGTGTTGGAACATGCAAGANTCTTAAAACGAGACAGTCAGGATTANGCC   240
241  ATACAAGAGATGTTCANTGGAAGTGANAGAGAGCCAAGTTTNGGTNCATTAACCAATCAA  300
301  ANGTGGATTGAAAAAGTCTTCANAAAA  326
```

GENETIC CONTROL OF FLOWERING

This invention relates to the genetic control of flowering in plants and the cloning and expression of genes involved therein. More particularly, the invention relates to the cloning and expression of the Late Elongated Hypocotyl (LHY) gene of *Arabidopsis thaliana*, and homologues from other species, and manipulation and use of the gene in plants.

BACKGROUND OF THE INVENTION

Efficient flowering in plants is important, particularly when the intended product is the flower or the seed produced therefrom. One aspect of this is the timing of flowering: advancing or retarding the onset of flowering can be useful to farmers and seed producers. An understanding of the genetic mechanisms which influence flowering provides a means for altering the flowering characteristics of the target plant. Species for which flowering is important to crop production are numerous, all crops which are grown from seed, with important examples being the cereals, rice and maize, probably the most agronomically important in warmer climatic zones, and wheat, barley, oats and rye in more temperate climates. Important seed products are oil seed rape and canola, sugar beet, maize, sunflower, soybean and sorghum. Many crops which are harvested for their roots or leaves are, of course, grown annually from seed and the production of seed of any kind is very dependent upon the ability of the plant to flower, to be pollinated and to set seed. Delaying flowering is important in increasing the yield of plants from which the roots or leaves are harvested. In horticulture, control of the timing of flowering is important. Horticultural plants whose flowering may be controlled include lettuce, endive, spinach and vegetable brassicas including cabbage, broccoli and cauliflower, and carnations and geraniums.

*Arabidopsis thaliana* is a facultative long day plant, flowering early under long days and late under short days. Because it has a small, well-characterized genome, is relatively easily transformed and regenerated and has a rapid growing cycle, Arabidopsis is an ideal model plant in which to study flowering and its control.

We have discovered that one of the genes required for this response to photoperiod is the Late Elongated Hypocotyl or LHY gene. We have found that plants carrying dominant gain of function mutations of the LHY gene flower later than their wild-types under long days but earlier than their wild-types under short days. We have now cloned and sequenced the LHY gene, which is provided herein, and demonstrated that the mutation causes the gene to be transcribed at higher levels than the wild-type gene. This suggests that increased expression of LHY delays flowering under long days.

BRIEF DESCRIPTION OF THE INVENTION

According to a first aspect of the present invention there is provided a nucleic acid molecule comprising a nucleotide sequence encoding a polypeptide with LHY function. Those skilled in the art will appreciate that "LHY function" may be used to refer to the ability to influence the timing of flowering phenotypically like the LHY gene of *Arabidopsis thaliana* (the timing being substantially unaffected by vernalisation). LHY mutants exhibit delayed flowering under long days, the timing of flowering being substantially unaffected by vernalisation. Also provided is a nucleotide sequence comprising the 5' non-coding region of a gene encoding a polypeptide with LHY function, preferably including substantially the whole promoter region of the gene, which gene may have the sequence of a LHY gene of *Arabidopsis thaliana*.

Further aspects based on the promoter region are disclosed below. However, discussion of mutation and manipulation of nucleic acid according to the invention encoding a LHY qene product (e.g. to make mutants etc., transform cells and plants and so on) applies mutatis mutandis to promoter nucleic acid according to the present invention.

Nucleic acid according to the present invention may have the sequence of a LHY gene of *Arabidopsis thaliana*, including coding and/or non-coding regions, or be a mutant, variant, derivative or allele of the sequence provided. Preferred mutants, variants, derivatives and alleles are those which encode a protein which retains a functional characteristic of the protein encoded by the wild-type gene, especially the ability to repress or delay flowering, for example by means of the regulation of other genes, as discussed herein.

A mutant, variant, derivative or allele in accordance with the present invention may have the ability to affect a physical characteristic of a plant, particularly a flowering characteristic. In various embodiments a mutant, variant, derivative or allele represses flowering compared with wild-type on expression in a plant, e.g. compared with the effect obtained using a gene sequence encoding the polypeptide of FIG. 1 (SEQ ID NO:2). "Repression" of flowering delays, retards, inhibits or slows it down. In other embodiments, a mutant, variant, derivative or allele promotes flowering compared with wild-type on expression in a plant, e.g. compared with the effect obtained using a gene sequence encoding the polypeptide of FIG. 1 (SEQ ID NO:2). "Promotion" of flowering advances, accelerates or brings it forward in time. Comparison of effect on flowering or other characteristic may be performed in *Arabidopsis thaliana*, although nucleic acid according to the present invention may be used in the production of a wide variety of plants and for influencing a characteristic thereof.

As discussed further below, over-expression of nucleic acid according to the present invention may delay flowering while under expression may promote flowering in a transgenic plant.

Changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid which make no difference to the encoded amino acid sequence are included, including changes to the non-coding regions such as the promoter or to binding sites for factors influencing regulation of gene expression.

A preferred nucleic acid sequence for a LHY gene is shown in FIG. 1 (SEQ ID NO:1), along with the predicted amino acid sequence of a polypeptide which has LHY function. Preferred nucleic acid according to the present invention encodes the amino acid sequence encoded by the sequence of nucleotides shown in FIG. 1 (SEQ ID NO:2).

A mutant, allele, variant or derivative amino acid sequence in accordance with the present invention may include within the sequence shown in FIG. 1 (SEQ ID NO:2), a single amino acid change with respect to the sequence shown in FIG. 1 (SEQ ID NO:2), or 2, 3, 4, 5, 6, 7, 8, or 9 changes, about 10, 15, 20, 30, 40 or 50 changes, or greater than about 50, 60, 70, 80 or 90 changes. In addition to one or more changes within the amino acid sequence shown in FIG. 1 (SEQ ID NO:2), a mutant, allele, variant or derivative amino acid sequence may include additional amino acids at the C-terminus and/or N-terminus.

A sequence related to a sequence specifically disclosed herein shares homology with that sequence. Homology may be at the nucleotide sequence and/or amino acid sequence level. Preferably, the nucleic acid and/or amino acid sequence shares homology with the coding sequence (SEQ ID NO:1) or the sequence encoded by the nucleotide sequence of FIG. 1 (SEQ ID NO:2), preferably at least about 50%, or 60%, or 70%, or 80% homology, most preferably at least about 90%, 95%, 96%, 97%, 98% or 99% homology.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art, or, and this may be preferred, the standard program BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman Homology may be over the full-length of the relevant sequence shown herein, or may more preferably be over a contiguous sequence of about or greater than about 20, 25, 30, 33, 40, 50, 67, 133, 167, 200, 233, 267, 300, 333, 400, 450, 500, 550, 600 or more amino acids or codons, compared with the relevant amino acid sequence or nucleotide sequence as the case may be.

Also provided by an aspect of the present invention is nucleic acid including or consisting essentially of a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a product able to influence a physical characteristic of a plant, particularly a flowering characteristic such as the timing of flowering. Preferred conditions for hybridisation are familiar to those skilled in the art, but are generally stringent enough for there to be positive hybridisation between the sequences of interest to the exclusion of other sequences.

The nucleic acid, which may contain for example DNA encoding the amino acid sequence of FIG. 1 (SEQ ID NO:2), as genomic or cDNA, may be in the form of a recombinant and preferably replicable vector, for example a plasmid, cosmid, phage or Agrobacterium binary vector. The nucleic acid may be under the control of an appropriate promoter or other regulatory elements for expression in a host cell such as a microbial, e.g. bacterial, or plant cell. In the case of genomic DNA, this may contain its own promoter or other regulatory elements and in the case of cDNA this may be under the control of an appropriate promoter or other regulatory elements for expression in the host cell.

A vector including nucleic acid according to the present invention need not include a promoter or other regulatory sequence, particularly if the vector is to be used to introduce the nucleic acid into cells for recombination into the genome.

Those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual*: 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711–8721 (1984)) and Guerineau and Mullineaux (1993) (Plant transformation and expression vectors. In: Plant Molecular Biology Labfax (Croy RRD ed) Oxford, BIOS Scientific Publishers, pp 121–148).

Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

Nucleic acid molecules and vectors according to the present invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may include cDNA, RNA, genomic DNA and may be wholly or partially synthetic. The term "isolate" encompasses all these possibilities. Where a DNA sequence is specified, e.g. with reference to a figure, unless context requires otherwise the RNA equivalent, with U substituted for T where it occurs, is encompassed.

The present invention also encompasses the expression product of any of the nucleic acid sequences disclosed and methods of making the expression product by expression from encoding nucleic acid therefore under suitable conditions, which may be in suitable host cells. Following expression, the product may be isolated from the expression system and may be used as desired, for instance in formulation of a composition including at least one additional component.

Purified LHY protein, or a fragment, mutant, derivative or variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes. Thus, the present invention provides a method of identifying or isolating a polypeptide with LHY function (in accordance with embodiments disclosed herein), comprising screening candidate polypeptides with a polypeptide comprising the antigen-binding domain of an antibody (for example whole antibody or a fragment thereof) which is able to bind an LHY polypeptide or fragment, variant or derivative thereof or preferably has binding specificity for such a polypeptide. Specific binding members such as antibodies and polypeptides comprising antigen binding domains of antibodies that bind and are preferably specific for a LHY polypeptide or mutant, variant or derivative thereof represent further aspects of the present invention, as do their use and methods which employ them.

Candidate polypeptides for screening may for instance be the products of an expression library created using nucleic acid derived from a plant of interest, or may be the product of a purification process from a natural source.

A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid, or by searching computer sequence databases, as discussed further below.

A further aspect of the present invention provides a method of identifying and cloning LHY homologues from plant species other than *Arabidopsis thaliana* which method employs a nucleotide sequence derived from that shown in FIG. 1 (SEQ ID NO:1). Sequences derived from these may themselves be used in identifying and in cloning other sequences. The nucleotide sequence information provided herein, or any part thereof, particularly in relation to the myb domain, may be used in a data-base search to find homologous sequences, expression products of which can be tested for ability to influence a flowering characteristic. These may have LHY function or the ability to repress flowering (especially under long days), preferably the timing of flowering being substantially unaffected by vernalisation, as disclosed herein. Alternatively, nucleic acid libraries may be screened using techniques well known to those skilled in the art and homologous sequences thereby identified then tested. Thus, a method of obtaining nucleic acid whose expression is able to influence a flowering characteristic of a plant is provided, comprising hybridisation of an oligonucleotide or a nucleic acid molecule comprising such an oligonucleotide to target/candidate nucleic acid. Target or candidate ucleic acid may, for example, comprise a genomic or cDNA library obtainable from an organism known to contain or suspected of containing such nucleic acid. Successful hybridisation may be identified and target/candidate nucleic acid isolated for further investigation and/or use.

Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further. It is well known in the art to increase stringency of hybridisation gradually until only a few positive clones remain.

As an alternative to probing, though still employing nucleic acid hybridisation, oligonucleotides designed to amplify DNA sequences may be used in PCR reactions or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers are sequences conserved (completely, substantially or partly) between at least two LHY polypeptides able to influence a flowering characteristic, such as timing of flowering. Other preferred primers are designed to amplify a region including a myb domain.

On the basis of amino acid sequence information oligonucleotide probes or primers may be designed, taking into account the degeneracy of the genetic code, and, where appropriate, codon usage of the organism from the candidate nucleic acid is derived.

Preferably an oligonucleotide in accordance with the present invention, e.g. for use in nucleic acid amplification, has about 10 or fewer codons (e.g. 6, 7 or 8), i.e. is about 30 or fewer nucleotides in length (e.g. 18, 21 or 24). Possible primers for amplifying a LHY wild-type or mutant gene include: 5'-ATGGATACTAATACATCT-3' (SEQ ID NO:3) and 5'-CTAGATTTAAAGATATTA-3' (SEQ ID NO:4). For amplifying the promoter, the primers LP1(SEQ ID NO:26) and LP2(SEQ ID NO:27) may be used (see below).

Assessment of whether or not a PCR product corresponds to a gene involved in the control of flowering may be conducted in various ways. A PCR band from such a reaction might contain a complex mix of products. Individual products may be cloned and each one individually screened. They may be analysed by transformation to assess function on introduction into a plant of interest.

The present invention also extends to nucleic acid encoding a LHY homologue obtained using a nucleotide sequence derived from that shown in FIG. 1 (SEQ ID NO:1), and uses thereof. No genes showing significant homology to LHY were identified in public databases, except for Expressed Sequence Tags (ESTs) of unknown function. However, a region of LHY (between amino acids 18 and 78) (SEQ ID NO:13) showed weak homology to several DNA binding proteins that contained a MYB domain (Frampton et al, 1989) careful analysis of this portion of the sequence of LHY demonstrated that this also probably contains a MYB domain. In particular, it is predicted to contain three alpha helices as discussed in Example 1 (FIG. 8). Unlike most MYB proteins, LHY contains a single MYB repeat, although other proteins containing a single MYB repeat were previously reported (Baranowski et al. 1994).

The provision of sequence information for the LHY gene of *Arabidopsis thaliana* enables the obtention of homologous sequences from other plant species. In particular, those skilled in the art may isolate LHY analogues from related, commercially important Brassica species (e.g. *Brassica nigra, Brassica napus* and *Brassica oleraceae*), as has been done for other flowering time genes isolated from Arabidopsis (e.g. CO; WO 96/14414).

Thus, included within the scope of the present invention are nucleic acid molecules which encode amino acid sequences which are homologues of LHY of *Arabidopsis thaliana*. Homology may be at the nucleic acid sequence or amino acid sequence level. Preferably, the nucleic acid or amino acid sequence shares homology with a sequence of FIG. 1 (SEQ ID NO:1 and SEQ ID NO:2), preferably at least about 50%, or at least about 60% or at least about 70% or at least about 80% homology, most preferably at least about 90% homology from species other than *Arabidopsis thaliana* and the encoded polypeptide shares a phenotype with the *Arabidopsis thaliana* LHY gene, preferably the ability to influence timing of flowering. These may promote or delay flowering compared with *Arabidopsis thaliana* LHY and mutants, variants or alleles may promote or delay flowering compared with wild-type. "Homology" may be used to refer to identity.

LHY gene homologues may also be identified from economically important monocotyledonous crop plants such as rice and maize. Although genes encoding the same protein in monocotyledonous and dicotyledonous plants show relatively little homology at the nucleotide level, amino acid sequences are conserved. In public sequence databases we recently identified several Arabidopsis cDNA clone sequences that were obtained in random sequencing programmes and share homology with LHY in regions of the protein that are known to be important for its activity. Similarly, a randomly sequenced rice cDNA showing strong homology to LHY was identified by homology, and should provide access to the LHY gene in economically important cereal plants. By sequencing each of these clones, studying their expression patterns and examining the effect of altering their expression, genes carrying out a similar function to LHY in regulating flowering time are obtainable. Of course, mutants, derivatives and alleles of these sequences are included in the scope of the present invention in the same terms as discussed above for the LHY gene.

In certain embodiments, nucleic acid according to the present invention encodes a polypeptide which has homology with all or part of the amino acid sequence shown in FIG. 1 (SEQ ID NO:2), in the terms discussed already above (e.g. for length), which homology is greater over the length of the relevant part (i.e. fragment) than the homology shared between a respective part of the amino acid sequence of FIG. 1 (SEQ ID NO:2) an EST sequence such as shown in Figure (SEQ ID NO:16 and SEQ ID NO:17), and may be greater than about 5% greater, more preferably greater than about 10% greater, more preferably greater than about 20% greater, and more preferably greater than about 30% greater. Thus, to exemplify with reference to one embodiment, nucleic acid encoding an amino acid mutant, variant or derivative of the amino acid sequence shown in FIG. 1 (SEQ ID NO:2) may be provided wherein the encoded amino acid sequence includes a contiguous sequence of about 100 amino acids which has greater homology with a contiguous sequence of 100 amino acids within the amino acid sequence of FIG. 1 (SEQ ID NO:2) than any contiguous sequence of 100 amino acids within an EST sequence such as shown in FIG. 9 (SEQ ID NO:16 and SEQ ID NO:17), preferably greater than about 5% greater homology, and so on.

Similarly, nucleic acid according to certain embodiments of the present invention may have homology with all or part of the nucleotide sequence shown in FIG. 1 (SEQ ID NO:1), in the terms discussed already above (e.g. for length), which homology is greater over the length of the relevant part (i.e. fragment) than the homology shared between a respective part of the nucleotide sequence of FIG. 1 (SEQ ID NO:1) and the encoding nucleotide sequence for an EST sequence such as shown in FIG. 9 (SEQ ID Nos:16 and 17) (accession numbers for which are given below) and may be greater than about 5% greater, more preferably greater than about 10% greater, more preferably greater than about 20% greater, and more preferably greater than about 30% greater. Thus, to exemplify with reference to one embodiment, nucleic acid may be provided in accordance with the present invention wherein the nucleotide sequence includes a contiguous sequence of about 300 nucleotides (or 100 codons) which has greater homology with a contiguous sequence of 300 nucleotides within the nucleotide sequence of FIG. 1 (SEQ ID NO:1) than any contiguous sequence of 100 nucleotides within the coding nucleotide sequence for an EST sequence such as shown in FIG. 9 (SEQ ID NO:16 and SEQ ID NO:17) (accession numbers for which are given below), preferably greater than about 5% greater homology, and so on.

Nucleic acid according to the present invention may include a nucleic acid sequence encoding a polypeptide which when expressed (e.g. at a high level) delays flowering, the timing of flowering being substantially unaffected by vernalisation. The delayed flowering may be under long days. The delay in flowering caused by LHY is a consequence of active over-expression of the gene and is therefore distinguished from that previously described for CO and LD in which loss of function results in delayed flowering. Expression of the LHY gene product, e.g. from the CaMV35S promoter, causes late flowering, whilst over-expression of the products of other genes identified in late flowering utants, such as CO, causes early flowering. The effect of expression fo the LHY gene may arise from the product actively repressing flowering under long days, or disrupting the functioning of a process required for early flowering, such as disruption of the circadian clock.

Vernalisation is low-temperature (e.g. from around −1° C. to around 6° C., usually just above 0° C.) treatment of plant (seedlings) or seed for a period of usually a few weeks or months, probably between about 30 days and about 60 days. It is a treatment required by some plant species before they will break bud or flower, simulating the effect of winter cold.

Also according to the present invention there is provided a plant cell having incorporated into its genome a heterologous sequence of nucleotides as provided by the present invention, under operative control of a regulatory sequence for control of expression. A further aspect of the present invention provides a method of making such a plant cell involving introduction of a vector comprising the sequence of nucleotides into a plant cell and causing or allowing recombination between the vector and the plant cell genome to introduce the sequence of nucleotides into the genome. A plant may be regenerated from one or more transformed plant cells.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser—see attached) other forms of direct DNA uptake (DE 4005152, WO 9012096, U.S. Pat. No. 4,684,611), liposome mediated DNA uptake (e.g. Freeman et al. *Plant Cell Physiol*. 29: 1353 (1984)), or the vortexing method (e.g. Kindle, *PNAS U.S.A*. 87: 1228 (1990d) Physical methods for the transformation of plant cells are reviewed in Oard, 1991, *Biotech. Adv*. 9: 1–11.

Agrobacterium transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072–1074; Zhang, et al. (1988) *Plant Cell Rep*. 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep*. 11, 585–591; Li, et al. (1993) *Plant Cell Rep*. 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, Agrobacterium mediated transformation is now emerging also as an highly efficient alternative transformation method in monocots (Hiei et al. (1994) *The Plant Journal* 6, 271–282).

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewd in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

DETAILED DESCRIPTION OF THE INVENTION

A LHY gene and a modified version thereof (allele, mutant, variant or derivative thereof), and other nucleic acid provided herein, including species homologues, may be used to affect a physical characteristic, such as a flowering characteristic which may include timing of flowering, in plants. For this purpose nucleic acid such as a vector as described herein may be used for the production of a transgenic plant. Such a plant may possess an altered flowering phenotype, particular in terms of timing of flowering, compared with wild-type (that is to say a plant that is wild-type for LHY or the relevant homologue thereof).

The invention further encompasses a host cell transformed with nucleic acid or a vector according to the present invention, especially a plant or a microbial cell. Thus, a host cell, such as a plant cell, including heterologous nucleic acid according to the present invention is provided. Within the cell, the nucleic acid may be incorporated within the chromosome. There may be more than one heterologous nucleotide sequence per haploid genome.

Also according to the invention there is provided a plant cell having incorporated into its genome nucleic acid, particularly heterologous nucleic acid, as provided by the present invention, under operative control of a regulatory sequence for control of expression. The coding sequence may be operably linked to one or more regulatory sequences which may be heterologous or foreign to the gene, such as not naturally associated with the gene for its expression. The nucleic acid according to the invention may be placed under the control of an externally inducible gene promoter to place expression under the control of the user.

A suitable inducible promoter is the GST-II-27 gene promoter which has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use, in a variety of tissues, including roots, leaves, stems and reproductive tissues.

Other suitable promoters include the Cauliflower Mosaic Virus 35S (CaMV 35S) gene promoter that is expressed at a high level in virtually all plant tissues (Benfey et al, 1990a and 1990b); the cauliflower meri 5 promoter that is expressed in the vegetative apical meristem as well as several well localised positions in the plant body, eg inner phloem, flower primordia, branching points in root and shoot (Medford, 1992; Medford et al, 1991) and the *Arabidopsis thaliana* LEAFY promoter that is expressed very early in flower development (Weigel et al, 1992).

Placing nucleic acid according to the present invention, such as a LHY gene or homologue, under the control of an externally inducible gene promoter thus placing the timing of flowering under the control of the user is advantageous in that, for example, flower production, and subsequent events such as seed set, may be timed to meet market demands, for example, in cut flowers or decorative flowering pot plants. Delaying flowering in pot plants is advantageous to lengthen the period available for transport of the product from the producer to the point of sale and lengthening of the flowering period is an obvious advantage to the purchaser.

In a further aspect the present invention provides a gene construct comprising an inducible promoter operatively linked to a nucleotide sequence provided by the present invention, such as the LHY gene of *Arabidopsis thaliana*, a homologue from another plant species, e.g. a Brassica such as *Brassica napus*, or any mutant, variant or allele thereof. As discussed, this enables control of expression of the gene. The present invention also provides plants transformed with said gene construct and methods comprising introduction of such a construct into a plant cell and/or induction of expression of a construct within a plant cell, by application of a suitable stimulus, an effective exogenous inducer.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

The term "heterologous" may be used to indicate that the gene/sequence of nucleotides in question have been introduced into said cells of the plant or an ancestor thereof, using genetic engineering, ie by human intervention. A transgenic plant cell, i.e. transgenic for the nucleic acid in question, may be provided. The transgene may be on an extra-genomic vector or incorporated, preferably stably, into the genome. A heterologous gene may replace an endogenous equivalent gene, ie one which normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher or lower activity than wild-type, may be used in place of the endogenous gene. Nucleic acid heterologous, or exogenous or foreign, to a plant cell may be non-naturally occuring in cells of that type, variety or species. Thus, nucleic acid may include a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant.

The invention further provides a method of influencing or affecting a physical e.g. flowering characteristic such as the timing of flowering of a plant, including causing or allowing expression of a heterologous nucleic acid sequence as discussed within cells of the plant.

The invention further provides a method of including expression from nucleic acid encoding the amino acid sequence of FIG. 1 (SEQ ID NO:2), or a mutant, variant, allele or derivative of the sequence, within cells of a plant (thereby producing the encoded polypeptide), following an earlier step of introduction of the nucleic acid into a cell of the plant or an ancestor thereof. Such a method may influence or affect a flowering characteristic of the plant, such as the timing of flowering. This may be used in combination with any other gene, such as transgenes involved in flowering or other phenotypic trait or desirable property.

The principal flowering characteristic which may be altered using the present invention is the timing of flowering. (Other physical characteristics of plants may be affected by means of expression from nucleic acid according to the present invention.) Over-expression of the gene product of the LHY gene leads to delayed flowering, particularly under long days (as suggested by the LHY mutant phenotype); under-expression may lead to precocious flowering. This degree of control is useful to ensure synchronous flowering of male and female parent lines in hybrid production, for example. Another use is to advance or retard the flowering in accordance with the dictates of the climate so as to extend or reduce the growing season. This may involve use of anti-sense or sense regulation.

In the present invention, over-expression may be achieved by introduction of the nucleotide sequence in a sense orientation. Thus, the present invention provides a method of influencing a flowering characteristic of a plant, the method comprising causing or allowing expression of the polypeptide encoded by the nucleotide sequence of nucleic acid according to the present invention from that nucleic acid within cells of the plant.

Under-expression of the gene product polypeptide may be achieved using anti-sense technology or "sense regulation" ("co-suppression").

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) Nature 334, 724–726; Zhang et al, (1992) The Plant Cell 4, 1575–1588, English et al., (1996) The Plant Cell 8, 179–188. Antisense technology is also reviewed in Bourque, (1995), Plant Science 105, 125–149, and Flavell, (1994) PNAS USA 91, 3490–3496.

An alternative is to use a copy of all or part of the target gene inserted in sense, that is the same, orientation as the target gene, to achieve reduction in expression of the target gene by co-suppression. See, for example, van der Krol et al., (1990) The Plant Cell 2, 291–299; Napoli et al., (1990) The Plant Cell 2, 279–289; Zhang et al., (1992) The Plant Cell 4, 1575–1588, and U.S. Pat. No. 5,231,020.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14–23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene.

Generally, the transcribed nucleic acid may represent a fragment of an LHY gene, such as including a nucleotide sequence shown in FIG. 1 (SEQ ID NO:1), or the complement thereof, or may be a mutant, derivative, variant or allele thereof, in similar terms as discussed above in relation to alterations being made to an LHY coding sequence and the homology of the altered sequence. The homology may be sufficient for the transcribed anti-sense RNA to hybridise with nucleic acid within cells of the plant, though irrespective of whether hybridisation takes place the desired effect is down-regulation of gene expression.

Thus, the present invention also provides a method of influencing a flowering characteristic of a plant, the method including causing or allowing anti-sense transcription from heterologous nucleic acid according to the invention within cells of the plant.

The present invention further provides the use of the nucleotide sequence of FIG. 1 (SEQ ID NO:2) or a fragment, mutant, derivative, allele, variant or homologue thereof for down-regulation of gene expression, particularly down-regulation of expression of an LHY gene or homologue thereof, preferably in order to influence a physical characteristic of a plant, especially a flowering characteristic such as the timing of flowering.

Anti-sense regulation may itself be regulated by employing an inducible promoter in an appropriate construct.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is well-reported in scientific and patent literature and is used routinely for gene control. See, for example, van der Krol, 1990; Napoli et al, 1990; Zhang et al, 1992.

Again, fragments, mutants and so on may be used in similar terms as described above for use in anti-sense regulation.

Thus, the present invention also provides a method of influencing a flowering characteristic of a plant, the method comprising causing or allowing expression from nucleic acid according to the invention within cells of the plant. This may be used to suppress activity of a polypeptide with ability to influence a flowering characteristic. Here the activity of the polypeptide is preferably suppressed as a result of under-expression within the plant cells.

Late Flowering Caused by Increased Expression of the LHY Gene

As described in Example 1, the lhy mutation causes late flowering under inductive long-day conditions and is caused by increased expression of the gene from a CaMV 35S promoter carried by a Ds transposon. This can therefore be considered as a transcriptional fusion, that was formed in vivo via transposition, between the CaMV 35S promoter and the LHY gene. This phenomenon was reported previously for a different gene (Wilson et al, 1996). An in vitro constructed fusion between the CaMV 35S promoter and the LHY gene, such that the LHY gene product is over expressed would be predicted to have the same effect. Example 2 demonstrates that introduction of the in vivo fusion between the CaMV 35S promoter and LHY into wild-type plants delays flowering under long days. This suggests that fusions between foreign promoters and the LHY gene could be used to delay flowering.

Causing Early Flowering by Reducing the Activity of LHY

The observation that increased expression of the LHY gene delays flowering suggests that the normal function of LHY might be to delay flowering, and that increasing the expression of the gene further enhances this effect. In this case, inactivating the LHY gene might be expected to cause early flowering. This could be done by classical chemical or radiation mutagenesis, by introducing constructs that express antisense copies of the LHY mRNA, by sense strand inactivation such as co-suppression or by expressing modified versions of the LHY protein.

The LHY promoter for which the sequence is given in FIG. 10 (SEQ ID NO:18) may be used in a number of ways, particularly when operably linked to a heterologous, exogenous or foreign transgene or fragment thereof. In essence the promoter may be used to regulate expression of any sequence of interest, its usefulness arising from its regulation in a circadian oscillatory manner.

For instance, a construct including the promoter (and any suitable mutant, variant, allele or derivative thereof, by way of addition, insertion, substitution and/or deletion of one or more nucleotides) may be used to control expression of a coding sequence or a sequence, either anti-sense or sense, for regulation particularly down-regulation of expression of a gene.

Thus genes may be expressed or down-regulated in the early morning but not at times of the day when they, or their down-regulation as the case may be, are not needed. This allows for energy reserves of a transgenic plant to be conserved. Furthermore, it allows for expression or down-regulation of genes in a manner which may avoid adverse side effects on a transgenic plant which effects may arise if the gene or down-regulation is constitutive.

An example of this is using a promoter according to the present invention to drive transcription of a sequence for down-regulation of the Mlo gene (Buschges, et al, 1997, CELL, 88, 695–705). Down-regulation of this barley gene or the equivalent homologue in other species provides broad spectrum mildew disease resistance. However, some alleles of mlo have associated negative effect on plant performance because they have a high level of localised necrotic response. Down-regulating mlo in an oscillatory manner may provide the desirable pathogen resistance without the undesirable side effect.

Other genes which may advantageously be expressed in a circadian rhythmic fashion using a promoter in accordance with the present invention include genes responsible for diverting metabolic resources into sink storage pathways e.g. starch, oil or other storage protein synthesis needed to be on or off during the day or night as appropriate, genes for improving night-time photorespiratory activity which are not needed during the day, gene used to modify photosynthesis during the day but not needed during the night, genes for protecting a plant from photinhibitory conditions, typically high light levels and low temperatures that occur often at dawn, and genes for modifying pigmentation, e.g. chlorophyll, anthocyanins, to achieve a cosmetically valuable change to the pigmentation pattern (e.g. stripey ornamentals).

Thus, according to a further aspect, the present invention provides a nucleic acid molecule encoding a LHY gene promoter.

In another aspect, the present invention provides a nucleic acid molecule encoding a promoter, the promoter including the promoter sequence of nucleotides shown in FIG. 10 (SEQ ID NO:18). Instead of using the full length promoter sequence, one or more fragments of the sequence shown in FIG. 10 (SEQ ID NO:18) may be used sufficient to promote gene expression in a plant in a circadian rhythymic fashion. The promoter may include or consist essentially of a sequence of up to about 1740 nucleotides 5' to coding sequence of the LHY gene in the *Arabidopsis thaliana* chromosome, or an equivalent sequence in another species. As noted, a fragment of this may be used, such as about 1700 nucleotides, 1600 nucleotides, 1500 nucleotides, 1400 nucleotides, 1300 nucleotides, 1200 nucleotides, 1100 nucleotides, 1000 nucleotides, 900 nucleotides, 800 nucleotides, 700 nucleotides, 600 nucleotides or 500 nucleotides, particularly a fragment within the sequence upstream from nucleotide 1059 in FIG. 10 (SEQ ID NO:18). The untranslated leader sequence at nucleotides 1059 to 1735 in FIG. 10 (SEQ ID NO:18) may be omitted. Of course, mutants, alleles, variants, derivatives and homologues may be employed in accordance with the present invention, as discussed.

Any of the sequences disclosed in the figures herein for a coding sequence according to the present invention may be used to construct a probe for use in identification and isolation of a promoter from a genomic library containing a genomic LHY gene (including homologues). Techniques and conditions for such probing are well known in the art and are discussed elsewhere herein. To find minimal elements or motifs responsible for temporal regulation, restriction enzyme or nucleases may be used to digest a nucleic acid molecule, followed by an appropriate assay (for example using a reporter gene such as luciferase) to determine the sequence required. A preferred embodiment of the present invention provides a nucleic acid isolate with the minimal nucleotide sequence shown in FIG. 10 (SEQ ID NO:18) required for circadian rhythmic promoter activity.

As noted, the promoter may include one or more sequence motifs or elements conferring circadian rhythmic regulatory control of expression. Other regulatory sequences may be included, for instance as identified by mutation or digest assay in an appropriate expression system or by sequence comparison with available information, e.g. using a computer to search on-line databases.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

The present invention extends to a promoter which has a nucleotide sequence which is allele, mutant, variant or derivative, by way of nucleotide addition, insertion, substitution or deletion of a promoter sequence as provided herein. Preferred levels of sequence homology with a provided sequence may be analogous to those set out above for encoding nucleic acid and polypeptides according to the present invention. Systematic or random mutagenesis of nucleic acid to make an alteration to the nucleotide sequence may be performed using any technique known to those skilled in the art. One or more alterations to a promoter sequence according to the present invention may increase or decrease promoter activity, or increase or decrease the magnitude of the effect of a substance able to modulate the promoter activity.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction. Use of a reporter gene facilitates determination of promoter activity by reference to protein production.

Further provided by the present invention is a nucleic acid construct including a promoter region as provided or a fragment, mutant, allele, derivative or variant thereof able to promoter transcription, operably linked to a heterologous gene, e.g. a coding sequence. A "heterologous" or "exogenous" gene is generally not a modified form of LHY. The gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a coloured product. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine gene activity. Examples of reporter genes commonly used in plants include the firefly luciferase gene (Millar, et al, 1992, The Plant Cell 4, 1075–1087) and the *E.coli* uidA gene (Jefferson, et al, 1987, EMBO J.6, 3901–3907). Any suitable reporter/assay may be used and it should be appreciated that no particular choice is essential to or a limitation of the present invention.

A promoter construct may be introduced into a cell using any technique previously described, e.g. to produce a stable cell line containing the construct integrated into the genome or for transient expression. Cells and plants etc. containing a promoter or construct and other methods and uses involving such as promoter or construct in accordance with the present invention are provided as aspects of the invention in the same terms as discussed above for other nucleic acid according to the invention.

Aspects and embodiments of the present invention will now be illustrated, by way of example, with reference to the accompanying figures. Further aspects and embodiments will be apparent to those skilled in the art. All documents mentioned in this text are incorporated herein by reference.

In the FIGURES:

FIG. 1 shows a nucleotide sequence (SEQ ID NO:1) according to one embodiment of the invention, being the sequence of the LHY ORF, obtained from *Arabidopsis thaliana*, with the predicted amino acid sequence (SEQ ID NO:2) shown below the coding region of said nucleotide sequence. The region underlined shows sequence which has been deleted in lhy mutants. The position of the insertion is indicated with a triangle.

FIG. 2: A graph showing the hypocotyl lengths of lhy mutant seedlings (2–4 leaves) and wild type grown on soil under different day lengths. Hypocotyl length in mm is shown for seedlings grown in the dark and under days of length 10, 16 and 24 hours light. Shaded bars are for lhy mutant seedlings; unshaded are for wild type.

FIG. 3(A–B): The sequence of IPCR fragments flanking the Ds in the lhy mutant. FIG. 3A: IPCR fragment derived from the 3' end of Ds (SEQ ID NO:5). FIG. 3B: IPCR fragment derived from the 5' end of Ds (SEQ ID NO:6).

Figure 4:
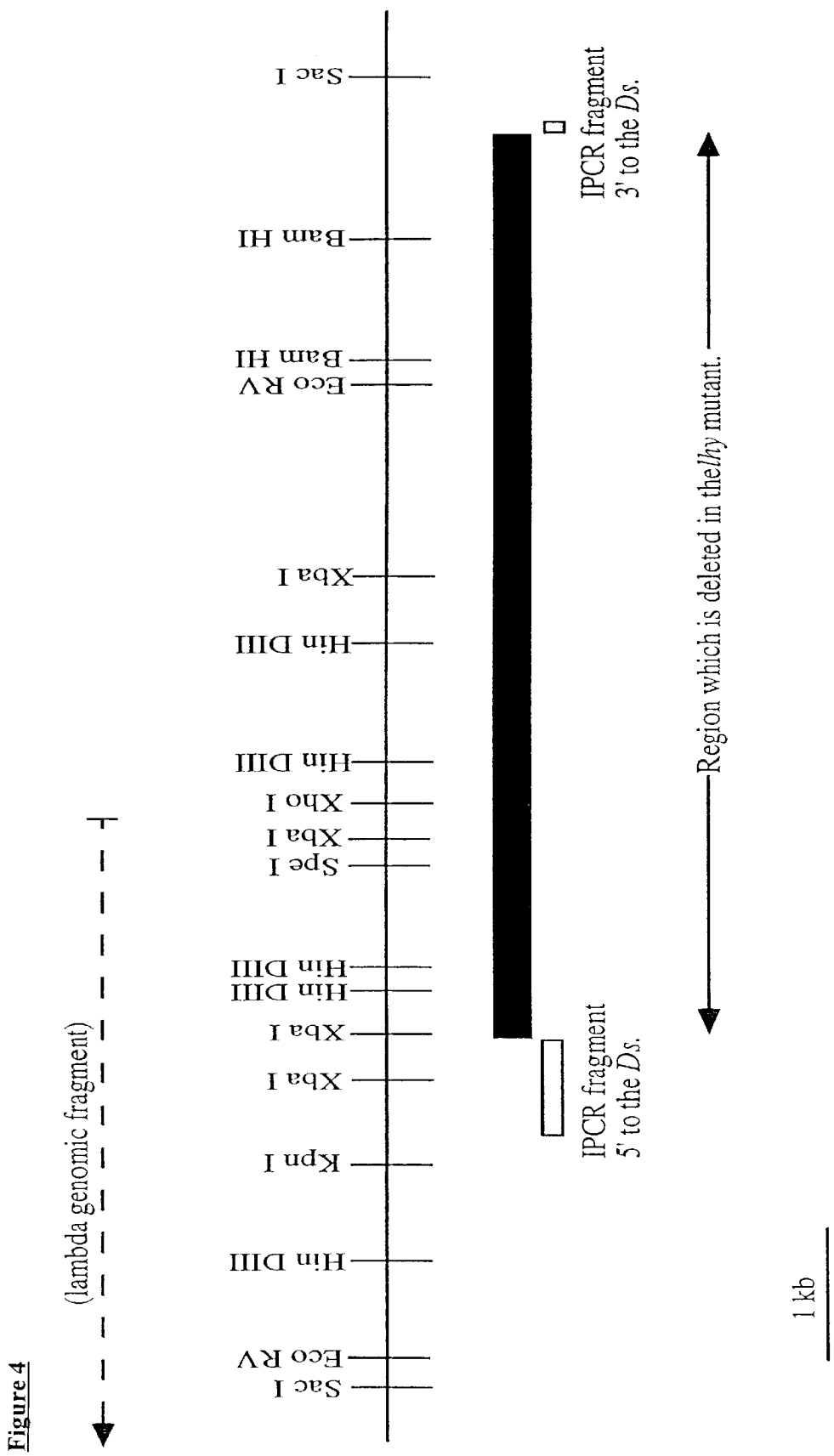

FIG. 4: A restriction enzyme map of the wild type LHY genomic locus and the deletion present in the lhy mutant.

Figure 5:
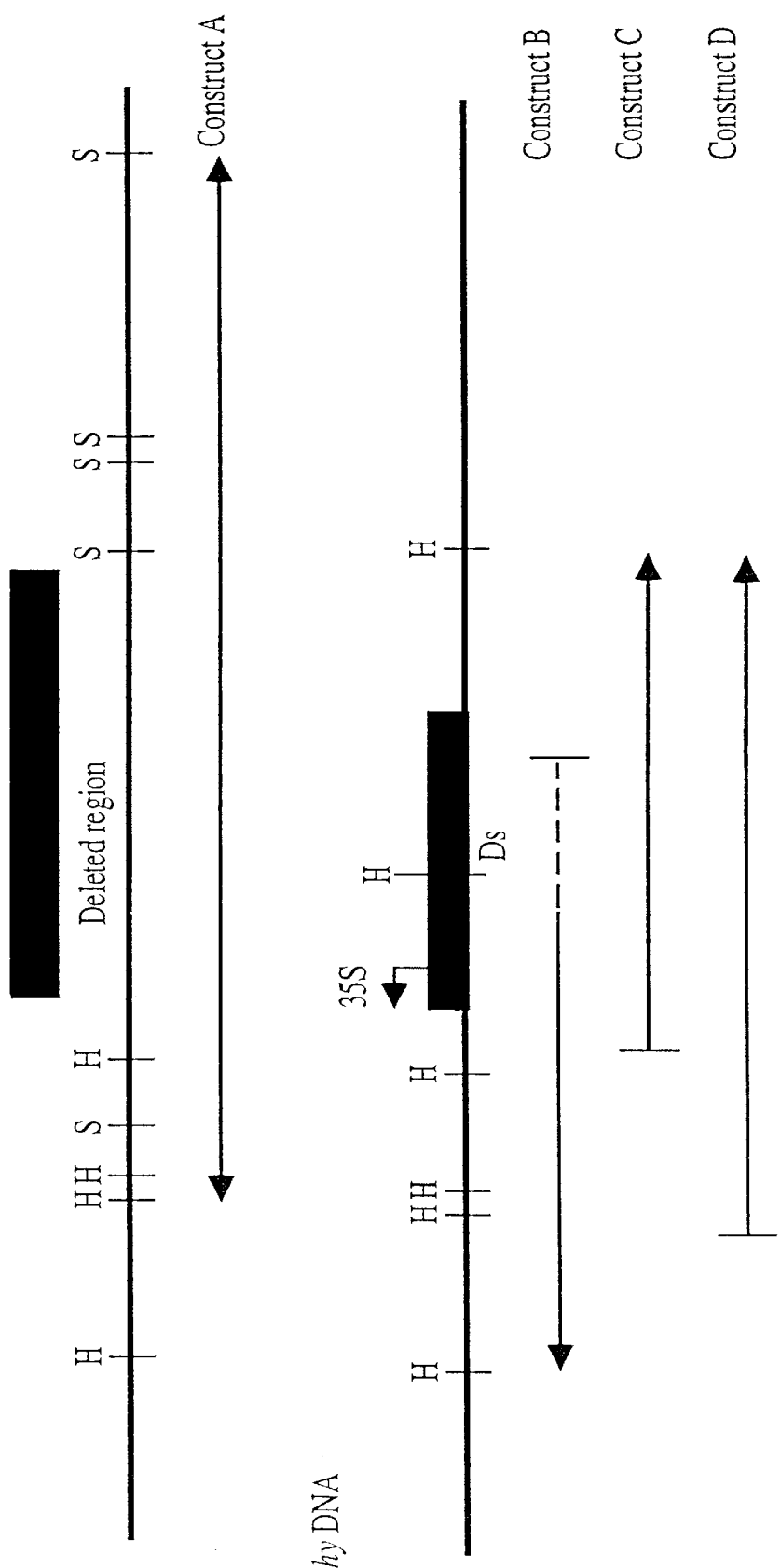

FIG. 5(A–B): The T-DNA constructs that were used in the complementation experiments and contain genomic DNA from the region surrounding the LHY gene.

FIG. 6A: Homology of the first 80 amino acids of LHY (SEQ ID NO:7) to the first alpha helix in the TEA domain of the peptides TEC1 (SEQ ID NO:8) and TEF1 (SEQ ID NO:9).

FIG. 6B: The homology of LHY to the myb domains in YCS3 (SEQ ID NO:10) and BAS1 (SEQ ID NO:11 and SEQ ID NO:12).

FIG. 7: The consensus sequence for a myb domain described in Frampton et al. (1989) with the corresponding LHY sequence underneath. Hash symbols represent hydrophobic residues and dollar symbols represent charged amino acids.

FIG. 8: The predicted alpha helices of the potential myb domain in LHY (SEQ ID NO:13). H indicates that the residue is likely to to be part of an alpha helix, and L indicates that the residue is likely to be part of a loop. The probability of forming a helix is shown below (Prob. H: 0=a very low probability; 9+a very high probability). The structure was predicted using the software Predict Protein (estimated to be greater than 70% accurate) (Rost et al. (1996))

FIG. 9: Two ESTs (SEQ ID NO:16 and SEQ ID NO:17) identified in the database which have homology to the LHY gene (SEQ ID NO:14 and SEQ ID NO:15).

FIG. 10 shows the genomic sequence of the promoter and untranslated leader of the LHY gene (SEQ ID NO:18). The ATG start codon (bases 1736–1738) of the LHY open reading frame is underlined. The longest LHY cDNA obtained starts at position 1059 (in bold and double underlined), indicating that the first 1059 bases include promoter sequence while that from 1059 to the ATG start codon encode the untranslated leader. There are sequences present in the genomic sequence of the untranslated leader and absent from the cDNA, which are introns that are spliced from the mRNA. The likely sequences of these introns are marked with italics in FIG. 10 (1228–1398; 1434–1592). The sequence GGATCC (16–21) denotes the BamHI site used to clone the promoter.

FIG. 11 shows the nucleotide sequence of EST 162I3T7, Accession no. R30439 (SEQ ID NO:19).

EXAMPLE 1

Cloning and Analysis of a LHY Gene Lambda and CDNA Libraries

A Lambda gt library containing Arabidopsis genomic DNA was obtained from Dr. N. Harberd (Whitelam et al. 1993). A cosmid library containing *Arabidopsis thaliana* genomic fragments in a plant transformable vector (T-DNA vector 04541) was obtained from Dr. C. Lister. 3 cDNA libraries were obtained from the Arabidopsis stock centre in Koln.

Identification of lhy in a Transposon Mutagenesis Screen.

The lhy mutant was identified in a two component Ac/Ds transposon mutagenesis screen, as described by Long et al.

(1993). It incorporated a modified stable Ac element containing a CaMV 35S promotor driven transposase gene. This stable Ac was used to mobilise a modified Ds element. The modified Ds contained a hygromycin resistance gene to allow easy identification of plants containing the Ds, and a CaMV 35S promotor reading out of the transposon at the 5' end. It has been shown that insertion of the Ds element into the proximity of a native gene can cause overexpression of that gene by the production of a gene fusion between the CaMV 35S promotor and the native gene (Wilson et al. 1996).

The mutagenesis strategy is can be summarised as follows: Plants homozygous for the Ds (marked by hygromycin resistance) were crossed with plants homozygous for the stable Ac containing transposase source (marked by β-glucoronidase gene. The F1 heterozygous plants were then allowed to self fertilise. In this generation the Ds may excise from the streptomycin gene in the T-DNA due to the presence of the transposase source in the Ac. occasionally it will reinsert somewhere in the genome and disrupt a native gene. F2 plants were selected for seedlings which contained an excised and reinserted, i.e. transposed, Ds, by selecting hygromycin and Streptomyin resistant seedlings. Such plants were selfed and the F3 plants were screened for mutations. This was a segregating population of plants ccontaining Ds and Ac. If the Ds has inserted into a gene then the progeny will also segregate with a mutant phenotype.

lhy mutants were identified in the F3 generation as Late flowering plants.

Description of the lhy Mutant Phenotype

When lhy mutants are grown under long days they flower later than wild type. As well as flowering late lhy mutants show other pleiotropic effects; their growth rate is reduced compared to wild type, lhy seedlings have an overall etiolated appearance, and if grown in darkness for three days have an exaggerated apical hook (similar to those of ethylene over expression mutants eg. etol van der Straeten et al.1993).

When grown under long day conditions lhy mutants flower with more vegetative leaves and later than wild type, as shown in Table 1. This is a completely dominant effect, with heterozygous plants flowering with exactly the same leaf number and at the same time as the homozygous plants. Under short day conditions lhy flowers slightly earlier than wild type making its response like that of other day neutral flowering time mutants eg. co (Koorneef et al.1991). However lhy produces leaves at a slower rate than wild type under both long and short days, so in terms of days to flower the lhy mutant flowers considerably later than wild-type under long days and at a similar time to wild-type under short days (Table 1). When the lhy mutant was grown under continuous light it flowered later than wild type.

lhy and wild type were vernalised for eight weeks at 4° C. and then moved to long day conditions to determine whether the flowering time of lhy was reverted to that of wild type. lhy flowered with an average of 9.96 leaves showing that although flowering occurs earlier than non vernalised plants, the effect of the mutation is not corrected by vernalisation (wild-type plants flower with an average of 6.52 leaves).

The rate of leaf development of lhy mutants and wild type was measured under long and short day lengths. Leaf counts were conducted every three days and the number of leaves over 3 mm in length were recorded. The rate of leaf development of wild type plants was constant under long and short days but that of the lhy mutant was much slower, than wild type under both conditions (Table 2). However when the plants were grown under continuous light the rate of leaf development in the lhy mutant increased to that of wild type.

The hypocotyl length of lhy and wt plants grown on soil, in different light conditions, was measured when the plants were at the two to four leaf stage. These were compared to plants grown in the dark on minimal MS media (FIG. 2). In wild type the hypocotyl length decreased noticably when plants were exposed to light. With lhy the hypocotyl does not elongate as much as wild type in dark conditions, but when lhy is grown under short days it has an elongated hypocotyl compared to wild type. This elongation seems to be dependant on the amount of light the seedlings receives because under continuous light the hypocotyl lengths of the mutant was similar to that of wild type.

The lhy mutant shows defective regulation of processes that are regulated by the endogenous circadian clock. In Arabidopsis rhythmic leaf movements and rhythmic expression of the CAB2 or CCR2 genes are often used to monitor the function of the circadian clock. We have shown that in lhy mutants leaf movements and the expression of the CAB2 and CCR2 genes are arrythmic, suggesting that in the lhy mutant the functioning of the circadian clock has been disrupted. The late flowering of the lhy mutant under long days may also be a consequence of disruption of clock function.

Cloning of the lhy Gene

To isolate the lhy gene, fragments of DNA adjacent to the Ds were obtained using Inverse PCR (IPCR). Primers specific for sequence at the termini of the Ds were used to amplify fragments by PCR. Pieces of DNA containing Ds sequence and small regions of the flanking genomic sequence were isolated. A second round of PCR was then performed with a second set of primers that were predicted to anneal to the PCR product to check that the correct fragment had been amplified. A fragment estimated to be 700 bp long was isolated 5' to the Ds, using BstY1 to digest mutant genomic DNA and the primers D74 and B34 for the initail amplification. Primers E4 and D73 were used for the second round. A fragment 200 bp long was isolated 3' to the Ds, by digesting genomic DNA with Sau3A and using the primers B39 and B38 for the initial PCR and then the primers D71 and DL4 for the second round. The IPCR fragments were than sequenced as seen in FIG. 3 (SEQ ID NO:5 and SEQ ID NO:6), and it was shown to contain the predicted Ds sequence.

Isolation of Larger Fragments of DNA in the Vicinity of the Ds.

A lambda phage gt library made from wild-type genomic DNA was probed using the IPCR fragment 5' to the Ds (SEQ ID NO:6). A lambda clone containing an llkb insert which strongly hybridised to the fragment 5' to the Ds was isolated. However when the IPCR fragment 3' to the Ds (SEQ ID NO:5) was used as a probe no hybridisation occurred. From this, and southern analysis of mutant and wild type DNA, it was concluded that a 7–8 kb deletion had occurred adjacent to the Ds. A genomic clone spanning this deletion was isolated from a cosmid library of wild-type DNA, and the region spanning the deletion was mapped with restriction enzymes (FIG. 4).

Identifying Genes in the Region Surrounding the Ds.

Three cDNAs were identified as hybridising to the region of the Ds and the deletion. In the mutant, the DNA encoding one of them had been totally deleted, the 3' end of a second was deleted and a small region of the 5' end of the third was deleted. It was concluded that the third cDNA was the most promising candidate for the LHY gene because only a small region of it had been deleted in the mutant and the Ds element was located at the 5' end of the gene in the orientation such that the CaMV 35S promoter within the transposon could transcribe the gene.

To identify which genes were causing the phenotype a complementation experiment was undertaken by introducing 3 constructs into wild type plants and one into the lhy mutant, to determine which of the candidate genes was the cause of the lhy mutation. Construct A contained DNA from wild-type plants that spanned the deletion and was obtained from a cosmid library. The other three constructs were obtained from DNA from the lhy mutant. Construct B contained the Ds and a region 5' to the insertion, Construct C contained the Ds and a region 3' to the insertion and construct D spanned the Ds and regions on both sides of the element (see FIG. 5). It was found that when constructs B and D were introduced into wild type plants a lhy mutant phenotype was recreated. See Example 2.

Gene Structure

The transformation results showed that a genomic region approximately 4 kb 5' to the Ds together with the adjacent Ds element is sufficient to cause the lhy mutant phenotype. This indicated that the cDNA encoded by this region, which hybridised to fragments 5' to the Ds, encoded the lhy gene. Also, as the mutation is dominant, it suggested that the lhy gene might be overexpressed in the mutant from the CaMV 35S promoter located at the 5' end of the Ds. The candidate cDNA was sequenced and a predicted 645 amino acid protein was identified (FIG. 1 (SEQ ID NO:1 and SEQ ID NO:2)).

When the predicted LHY protein was compared to known protein sequences in the Swissprot database by a fasta homology search, the first 80 amino acids showed homology to the first alpha helix of the TEA domain of TEC1 (SEQ ID NO:8) and TEF1 (SEQ ID NO:9) around the region of the first alpha helix and weak homology to a number of myb DNA binding proteins (FIG. 6). The yeast myb proteins YCS3 (SEQ ID NO:10) (Accession no. P25357), showed 14/41 identity and 24/41 similarity to the myb domain in LHY and the first myb domain in BAS1 (SEQ ID NO:11 and SEQ ID NO:12), (Accesion no. P22035) showed 12/38 identity and 21/38 similarity to the myb domain in LHY.

A classical myb domain consists of three myb repeats, each myb repeat contains three alpha helices which are defined by evenly spaced tryptophan residues. The first helix is thought to be involved in a protein-protein interaction, with the second and third showing a helix-turn-helix DNA binding motif. Not all myb proteins have this classical structure, some only have one or two myb repeats. Also the third tryptophan in the third alpha helix is not always conservered. At the amino acid level myb domains are not strongly conserved, it is the overall nature of the sequence which is important (Frampton et al. 1989), they should have correctly spaced hydrophobic amino acids and three alpha helicies.

The predicted LHY protein only contains a single myb repeat (amino acid residues 18–78) (SEQ ID NO:13) which has the first two tryptophan residues with the correct spacing as can be seen in FIG. 7 (from Frampton et al 1989) but the third tryptophan is absent. The amino acid sequence in this predicted myb domain was analysed with a structure prediction package (predict protein) available on the Internet at the EMBL-Heidelberg web site. For these 60 amino acids there was the highest prediction of three alpha helicies (FIG. 8), supporting the presence of a single myb domain in LHY. The presence of a myb domain suggests that LHY functions by binding to DNA, and might therefore regulate the expression of other genes.

Comparison of lhy to Other Sequences in the Databases.

The predicted protein encoded by the LHY gene was compared to other sequences in the Gen-bank Expressed Sequence Tags (EST) database using the Tfasta software available on the Wisconsin software package. This program translates all the sequences in the databases into possible proteins (using all six open reading frames) and comparing them to the sequence in question. One EST showed 100% homology to the 3' end of the LHY transcript (EST clone 162I3T7, Accession no. R30439). This is probably a truncated cDNA of the LHY gene. Its sequence is shown in FIG. 11 (SEQ ID NO:19). It is only 447 bp. A second (SEQ ID NO:16) showed significant homology (54% identity, 93% similarity) to the predicted myb DNA binding region in lhy. (EST 157C23T7, Accession no. T88489) The complete sequence of this second EST has not been elucidated yet so it is unknown whether it has homology to LHY in other parts of the gene (see FIG. 9A).

LHY also showed homology (34% identity, 93% homology) to a rice EST (SEQ ID NO:17). EST OSS15442A (Accesion no. D48887) showed two regions of strong homology to the 3' end of the gene, indicating it might be a truncated cDNA. (FIG. 9B)

Expression of the lhy Gene

RNA from lhy and wild type plants was blotted, onto nitrocellulose and probed with the LHY gene. The levels of transcript in lhy was at a much higher level than wild type. To test whether this expression was due to a gene fusion between the gene and the CaMV 35S promoter, RT-PCR was conducted on a sample of RNA from lhy using primers specific for the 5' end of the Ds and the LHY transcript. A fragment of DNA was produced which corresponded to the cDNA sequence. This was confirmed by Southern analysis using the LHY gene as a probe.

Native LHY Expression.

The lhy mutant showed a daylength insensitive phenotype, and therefore there was a possibility that LHY expression is controlled by daylength. RNA was extracted from plants which had been grown under long days (16 hours light) and short days (10 hours light) and harvested every two hours from the beginning of the light period for twenty four hours and then the plants were put into total darkness for a further 48 hours. This analysis demonstrated that the LHY transcript is likely to be circadian rhythm controlled, increasing in the night to a peak when the lights come on and then decreasing slowly. This cycling continues in the absence of light indicating that the gene is circadian rhythm controlled.

The transcript levels were compared for long and short day grown plants and were found to be higher and lasted for longer under short day conditions than under long days. However the transcript levels in wild type never reached the levels of that in lhy. It remains to be tested whether the late flowering in lhy is due to higher expression of LHY or having the transcript present for a longer period.

To determine when LHY is first expressed developmentally, seeds were sown in MS minimal media under LD conditions and harvested at 2 hours after the light came on, once a day for eight days. It was found that with the germinating seeds the transcript was detectable after two days, indicating that it is first expressed early in seedling development. Three batches of seeds were also germinated in total darkness for two weeks and the first lot harvested immediately, the second lot after 2 hours light, and the third lot after 24 hours of a Long day cycle. No transcript was detected in the first two samples and faint expression was detected in the third sample, indicating the presence of light is needed to switch the transcript on.

Location of LHY in the Genome

The location of LHY was demonstrated by showing that the CAPS markers (Konieczny and Ausubel, 1993) PVV4 and NCC1 are genetically linked to the mutation. LHY was mapped 1.8 cM from the marker PVV4. No mutation affecting flowering time was previously mapped to this position.

METHODS

Growth Conditions and Measurement of Flowering Time

Flowering time was measured under defined conditions by growing plants in Sanyo Gallenkamp Controlled Environment rooms at 20° C. Short days comprised a photoperiod of 10 hours lit with 400 Watt metal halide power star lamps supplemented with 100 watt tungsten halide lamps. This provided a level of photosynthetically active radiation (PAR) of 113.7 µmoles photons $m^{-2}s^{-1}$ and a red:far red light ration of 2.41. A similar cabinet and lamps were used for the long day. The photoperiod was for 10 hours under the same conditions used for short days and extended for a further 8 hours using only the tungsten halide lamps. In this cabinet the combination of lamps used for the 10 hour period provided a PAR of 92.9 µmoles photons $m^{-2}s^{-1}$ and a red:far red ratio of 1.49. The 8 hour extension produced PAR of 14.27 µmoles $m^{-2}s^{-1}$ and a red:far-red ratio of 0.66.

The flowering times of large populations of plants were measured in the greenhouse. In the summer the plants were simply grown in sunlight. In winter supplementary light was provided so that the minumum daylength was 16 hours.

To measure flowering time, seeds were placed at 4° C. on wet filter paper for 4 days to break dormancy and were then sown on soil. Germinating seedlings were usually covered with cling film or propagator lids for the first 1–2 weeks to prevent dehydration. Flowering time was measured by counting the number of leaves, excluding the cotyledons, in the rosette at the time the flower bud was visible. Leaf numbers are shown with the standard error at 95% confidence limits. The number of days from sowing to the appearance of the flower bud was also recorded, but is not shown.

Plant Material

The standard wild-type genotype used was *Arabidopsis thaliana* Landsberg erecta.

Isolation of Plant Genomic DNA.

Plant genomic DNA was isolated from glasshouse grown plants essentially as described by Tai and Tanksley, Plant Mol. Biol. Rep. 8: 297–303 (1991), except that the tissue was ground in liquid nitrogen and the RNase step omitted. Large-scale (2.5–5 g leaves) and miniprep (3–4 leaves) DNA was prepared using this method.

Gel Blotting and Hybridisation Conditions.

Gel transfer to Hybond-N, hybridisation and washing conditions were according to the manufacturer's instructions, except that DNA was fixed to the filters by UV Stratalinker treatment (1200 uJ×100; Stratagene) and/or baked at 80° C. for 2 h. Radiolabelled DNA was prepared by random hexamer labelling.

Inverse Polymerase Chain Reaction (IPCR)

IPCR was used to isolate DNA adjacent to the Ds. The DNA from the lhy mutant was cleaved using the restriction enzymes Bst Y1 for the 5' end and Sau 3A for the 3' end and then treated as described in Long et al. (1993) The Primers used to amplify the DNA at the 5' end of the Ds were the same as those described in Wilson et al. 1996 (D74 and B34 for the first round and E4 and D73 in the second round) For the 3' end primers B38 (5'-GATATACCGGTAA-CGAAAACGAACGG) (SEQ ID NO:20) and B39 (5'-TTCGTTTCCGTCCCGCAAGTTAAATA) (SEQ ID NO:21) were used in the first round and primers D71 (5'-CGTTACCGACCGTTTTTCATCCCTA) (SEQ ID NO:22) and D75 (5'-ACGAACGGGAT-AAATACGGTAATC) (SEQ ID NO:23) were used in the second round.

RNA Extractions

RNA was extracted using a method which is a modified version of that described by Stiekma et al (1988). Approximately 5 g of tissue frozen in liquid nitrogen was ground in a coffee grinder and extracted with a mixture of 15 ml of phenol and 15 ml of extraction buffer (50 mM Tris pH8, 1 mM EDTA, 1% SDS). The mixture was shaken, centrifuged and 25 ml of the aqueous layer recovered. This was then shaken vigorously with a mixture of 0.7 ml 4M sodium chloride, 10 ml phenol and 10 ml of chloroform. The aqueous layer was recovered after centrifugation and extracted with 25 ml of chloroform. The RNA was then precipitated from 25 ml of the aqueous layer by the addition of 2 ml of 10 M LiCL, and the precipitate recovered by centrifugation. The pellet was dissolved in 2 ml DEPC water and the RNA precipitated by the addition of 0.2 ml of 4M sodium chloride and 4 ml of ethanol. After centrifugation the pellet was dissolved in 0.5 ml of DEPC water and the RNA concentration determined.

DNA Extractions

Arabidopsis DNA was performed by a CTAB extraction method described by Dean et al (1992).

Isolation of cDNA by RT-PCR

Total RNA was isolated from whole seedlings at the 2–3 leaf stage growing under long days in the greenhouse. For first strand cDNA synthesis, 10 ug of RNA in a volume of 10 ul was heated to 65° C. for 3 minutes, and then quickly cooled on ice. 10 ul of reaction mix was made containing 1 ul of RNAsin, 1 ul of standard $dT_{17}$-adapter primer (1 ug/ul; Frohman et al, 1988), 4 ul of S×reverse transcriptase buffer (250 mM TrisHCl pH8.3, 375 mM KCl, 15 mM $MgCl_2$), 2 ul DTT (100 mM), 1 ul dNTP (20 mM), 1 ul reverse transcriptase (200 units, M-MLV Gibco). This reaction mix was then added to the RNA creating a final volume of 20 ul. The mixture was incubated at 42° C. for 2 hours and then diluted to 200 ul with water.

10 ul of the diluted first strand synthesis reaction was added to 90 ul of PCR mix containing 4 ul 2.5 mM dNTP, 10 ul 10×PCR buffer (Boehringer plus Mg), 1 ul of a 100 ng/ul solution of each of the primers, 73.7 ul of water and 0.3 ul of 5 units/ul Taq polymerase (Boehringer or Cetus Amplitaq). The primers used D73 (5'-GTTAGTTTTATCCCGATCGATTTCGA) (SEQ ID NO:24) and CaRIC7F (5'-ACCGCTTT-GATTGAGAAGCTG) (SEQ ID NO:25). The reaction was performed at 94° C. for 1 minute, 34 cycles of 55° C. for 1 minute, 72° C. for 2 minutes and then finally at 72° C. for 10 minutes.

20 ul of the reaction was separated through an agarose gel, and the presence of a fragment of the expected size was demonstrated after staining with ethidium bromide. The DNA was transferred to a filter, and the fragment of interest was shown to hybridise to a short DNA fragment derived from the LHY gene.

DNA Sequencing

The Sanger method was used to sequence fragments of interest inserted in a Bluescript plasmid vector. Reactions were performed using a Sequenase kit (United States Biochemical Corporation).

Screening Phage and Cosmid Libraries

A lysate of the cosmid library (Olszewski and Ausubel, 1988) was used to infect *E. coli* DH5 alpha, and twenty thousand colonies were screened with the probes described in the text. Three cDNA libraries were screened to try to identify a CO cDNA. The number of plaques screened were $5\times10^5$ from the "aerial parts" library (supplied by EC Arabidopsis Stock Center, MPI, Cologne), $3\times10^5$ plaques of a library made from plants growing in sterile beakers (supplied by the EC Arabidopsis Stock Center) and $1\times10^6$ plaques of the CD4-71-PRL2 library (supplied by the Arabidopsis Biological Resource Center at Ohio State University).

Transformation of Arabidopsis

The cosmids containing DNA from the vicinity of LHY were mobilised into *Agrobacterium tumefaciens* C58C1, and the T-DNA introduced into Arabidopsis plants as described by Valvekens et al, 1988. Roots of plants grown in vitro were isolated and grown on callus-inducing medium (Valvekens et al, 1988) for 2 days. The roots were then cut into short segments and co-cultivated with *Agrobacterium tumefaciens* carrying the plasmid of interest. The root explants were dried on blotting paper and placed onto callus-inducing medium for 2–3 days. The Agrobacterium were washed off, the roots dried and placed onto shoot inducing medium (Valvekens et al, 1988) containing vancomycin to kill the Agrobacterium and kanamycin to select for transformed plant cells. After approximately 6 weeks green calli on the roots start to produce shoots. These are removed and placed in petri dishes or magenta pots containing germination medium (Valvekens.et al, 1988). These plants produce seeds in the magenta pots. These are then sown on germination medium containing kanamycin to identify transformed seedlings containing the transgene (Valvekens et al, 1988).

EXAMPLE 2

Delaying Flowering of Wild-type Plants by Introducing a Copy of the LHY Gene Fused to the CaMV 35S Promoter As described in Example 1, introducing constructs B or D (FIG. 5) into wild-type plants was sufficient to cause the lhy mutant phenotype. This was used to identify the LHY gene, because it indicated that the gene must be located on the region of overlap between the two cosmids. Sequence and transcript analysis demonstrated that LHY was the only gene located in this interval, and that it was over-expressed in the mutant. Introduction of a fusion of the CaMV 35S promoter to the LHY gene into wild-type plants is therefore sufficient to delay flowering, and this fusion causes the mutant phenotype even in the presence of two copies of the wild-type gene.

The lhy mutation has other effects on plant growth and development, as well as delaying flowering time. For example, it causes a reduction in chlorophyll content and an elongated hypocotyl. The use of promoters other than the CaMV35S promoter to drive over-expression of LHY, or regulation of the timing of over-expression of LHY mAY allow the separation of the repression of flowering from the other pleiotropic effects. For example the meri5 (Medford et al, 1991) or shootmeristemless (Long et al, 1996) promoters could be used to drive LHY expression specifically in the shoot meristem. Assuming that LHY encodes a transcription factor, a protein fusion between the LHY gene and a steroid binding site, such as that of the rat glucorticoid receptor (Lloyd et al, 1994), and expression of the fusion from the CaMV 35S promoter would LHY activity to be regulated. This would allow over-expression of the gene to be activated at certain times in development, and therefore repression of flowering to be initiated later in development. This might, for example, enable flowering to be delayed without the effects of the mutation on hypocotyl elongation.

The genomic sequence of the promoter and untranslated leader of the LHY gene is shown in FIG. 10 (SEQ ID NO:18).

The ATG start codon (bases 1740–1742) of the LHY open reading frame is underlined. The longest LHY CDNA that has been obtained starts at position 1079 (in bold and underlined); indicating that the the first 1079 bases probably encode promoter sequence while that from 1079 to the ATG start codon encode the untranslated leader. The region shown in italics from position 1225 to 1370 is present in the genomic sequence but not the cDNA and represents an intron within the untranslated leader sequence.

The promoter and untranslated leader were cloned by using PCR to amplify the region from a plasmid carrying a larger fragment of the LHY gene. A proof reading polymerase was used to reduce the error rate during amplification. The primers used were LP1 (CATCAACGTAGGGATCCGTGAAATAT) (SEQ ID NO:26) which anneals at the 5' end of the promoter region from bases 5 to 30 in the sequence shown in FIG. 10. The bases underlined (16–21) represent the BamHI site that was subsequently used to clone the amplified fragment, and those bases double underlined were errors introduced into the LP1 primer to introduce the BamHI site. The second primer used was LP2 (GGACTAGTAACAGGACCGGTTGCAGCTATTC) (SEQ ID NO:27) which anneals immediately upstream of the ATG and introduces a SpeI site. A fragment of the expected size was amplified with these primers and inserted into Bluescript vector cleaved with SpeI and BamHI. The DNA sequence of the cloned fragment was then determined and found to be that expected.

The promoter may be used to drive gene expression in a circadian-regulated manner similar to that shown by the LHY gene. For instance, it may be used to drive expression of firefly luciferase. The vector VIP11omeFFLuc which was previously described by Anderson et al (1994) and Anderson and Kay (1995) may be used for this. The vector contains BamHI and HindIII sites upstream of the luciferase gene. Bluescript plasmid carrying the LHY promoter fragment described above is cleaved with SpeI and partially filled in with Klenow polymerase to make it compatible with a partially filled in HindIII site. The plasmid is then cleaved with BamHI. The vector is cleaved with HindIII, partially filled in and cleaved with BamHI. This enables insertion of the LHY promoter fragment into the vector such that it drives luciferase expression. This construct is introduced into Agrobacterium, and these bacteria used to introduce the T-DNA into Arabidopsis by selection of kanamycin resistance. In the transgenic plants expression of luciferase may be used to show the promoter fragment driving circadian rhythm-regulated gene expression as has been shown previously for the promoter of the CAB2 gene of Arabidopsis (Millar et al, 1992).

The promoter may be used to drive other gene products in this way. This enables gene products of interest to be expressed around dawn. This is an advantage if plant growth and development is disrupted by the gene product when it is constantly expressed, for example because it is harmful to the cell during extended exposure to light or darkness. It also enables the gene product to interact with gene products present at the same time during the circadian cycle, and not to interact with those present at different times during the cycle.

REFERENCES

Anderson et al (1994) Plant Journal 6, 457–470.
Anderson and Kay (1995) PNAS USA 92, 1500–1504.
Baranowskij et al, (1994) EMBO J. 13, 5383–5392.
Frampton et al., (1989) Nature 342, 134.
Koornneef et al., (1991) Mol Gen Genet 229, 57–66.

Konieczny and Ausubel (1993) Plant J. 4, 403–410.
Lister and Dean, (1993) Plant J. 4, 745–750.
Lloyd et al (1994) Science 266, 436–439.
Long et al., (1993) Proc. Natl. Acad. Sci. USA 90,10370–10374.
Long et al, (1996) Nature 379, 66–69.
Medford et al (1991) Plant Cell 3, 359–370.
Millar et al (1992) The Plant Cell 3, 541–550.
Napoli et al., (1990) The Plant Cell 2, 279–289.
Olszewski, N. and Ausubel, F. M. (1988) Nucleic Acids Res. 16, 10765–10782.
Rost et al (1996) Meth. in enzym. 266, 525–539
Rothstein et al., (1987) Proc. Natl. Acad. Sci. USA 84, 8439–8443.
Smith et al., (1988) Nature 334, 724–726.
Stam, (1993) Plant J. 3, 739–744.
Stiekema et al., (1988) Plant Molecular Biology 11, 255–269.
Tai T, Tanksley S (1991) Plant Mol Biol Rep.8,297–303.
van der Krol et al., (1990) The Plant Cell 2, 291–229.
van der Staeten et al., (1993) Plant Physiol. 102, 401–408.
Whitelam et al., (1993) Plant Cell 5, 757–768.
Zhang et al., (1992) The Plant Cell 4, 1575–1588.

TABLES

Flowering times and growth rates of lhy mutant and wild-type plants. Flowering times are shown as leaf numbers at flowering, and were measured in two experiments independently. The Table describing Experiment 2 illustrates that the mutation is dominant; plants heterozygous for the lhy mutation flower at the same time as those that are homozygous for the mutation. Growth rate is shown as number of leaves formed each day, and is significantly slower for lhy than for wild-type plants grown under short days.

TABLE 1

Flowering time of lhy mutants under long and short days.

| Genotype and Daylength | No. rosette leaves | No. cauline leaves | Total no. leaves |
|---|---|---|---|
| A. Number of rosette and cauline leaves formed by lhy mutants under long and short days. | | | |
| lhy (LD) | 12.0 (+/−0.5) | 5.0 (+/−0.3) | 17.0 (+/−0.7) |
| lhy (SD) | 14.6 (+/−0.4) | 4.3 (+/−0.2) | 18.9 (+/−0.4) |
| Landsberg erecta (LD) | 4.6 (+/−0.2) | 2.8 (+/−0.1) | 7.4 (+/−0.2) |
| Landsberg erecta (SD) | 27.4 (+/−0.5) | 9.7 (+/−0.3) | 37.0 (+/−0.5) |

| B. Flowering time of lhy mutants. | | |
|---|---|---|
| Genotype and Daylength | Time to flowering (Days) | Total no. leaves at flowering |
| lhy (LD) | 33.2 (+/−1.8) | 13.5 (+/−1.9) |
| lhy (SD) | 36.8 (+/−1.7) | 11.2 (+/−1.2) |
| Landsberg erecta (LD) | 20.1 (+/−1.5) | 6.6 (+/−0.7) |
| Landsberg erecta (SD) | 35.6 (+/−1.7) | 19.6 (+/−2.2) |

TABLE 2

Rate of leaf formation of lhy and wild type.

| | lhy | | wt | |
|---|---|---|---|---|
| Conditions | Rate lves/day | LR | Rate lves/day | LR |
| Long days | 0.85 | 0.997 | | |
| Short days | 0.52 | 0.995 | 1.05 | 0.999 |

What is claimed is:

1. An isolated polynucleotide nucleic acid isolate encoding a polypeptide which comprises the amino acid sequence shown in FIG. 1 (SEQ ID NO: 2) and has the functional activity of the polypeptide of SEQ ID NO: 2, which functional activity is delaying flowering time.

2. A polynucleotide according to claim 1 wherein the coding nucleotide sequence is the coding nucleotide sequence shown in FIG. 1 (SEQ ID NO:1).

3. A polynucleotide according to claim 1 operably linked to a regulatory sequence for expression.

4. An isolated polynucleotide which comprises a nucleotide sequence complementary to 300 contiguous nucleotides of the sequence of claim 1.

5. A method of producing a plant, the method including incorporating a heterologous polynucleotide according to claim 4 into a plant cell and regenerating a plant from said plant cell.

6. A method of advancing flowering time of a plant, the method including causing or allowing expression from a polynucleotide according to claim 4 within cells of the plant.

7. A polynucleotide according to claim 1 operably linked to a regulatory sequence for transcription.

8. A polynucleotide according to claim 7 wherein the regulatory sequence includes an inducible promoter.

9. A nucleic acid vector suitable for transformation of a plant or microbial host and including a polynucleotide according to claim 1.

10. A plant or microbial cell containing a heterologous polynucleotide or nucleic acid vector according to claim 9.

11. A plant including a cell according to claim 10.

12. A part or propagule of a plant including a cell according to claim 10.

13. A method of producing a plant, the method including incorporating a heterologous polynucleotide according to claim 1 into a plant cell and regenerating a plant from said plant cell.

14. A method according to claim 13 or claim 5 including sexually or asexually propagating or growing off-spring or a descendent of said plant, wherein said off-spring or descendant comprises said heterologous polynucleotide.

15. A method of delaying flowering time of a plant, the method including causing or allowing expression of a product encoded by a heterologous polynucleotide according to claim 1 within cells of the plant.

* * * * *

SEQUENCE LISTING

<160> NUMBER OF SEQ ID NOS: 27

<210> SEQ ID NO 1
<211> LENGTH: 2526
<212> TYPE: DNA
<213> ORGANISM: Arabidopsis thaliana
<220> FEATURE:
<221> NAME/KEY: CDS
<222> LOCATION: (338)..(2275)

<400> SEQUENCE: 1

```
cagttatctt cttccttctt ctctctgttt tttaaattta ttttagaga atttttttg      60 ttttgcttcc gatttgatta tttccgggaa cgatgacttc tccggggagt tcccggtgag   120
atgataagtc agattgcata cttgtctcct ccatggctac tctcaagggt tttggctgcg   180
gtggattcgt ttggtttctc tagaatctaa agaggttatc acaacggctt tgcaatttga   240
aaactttcat gtttggggag atcaaagatg gtttcttttt tatactttac ttgttagaga   300
ggatttgaag cagcgaatag ctgcaaccgg tcctgtt atg gat act aat aca tct    355
                                       Met Asp Thr Asn Thr Ser
                                         1               5 gga gaa gaa tta tta gct aag gca aga aag cca tat aca ata aca aag    403
Gly Glu Glu Leu Leu Ala Lys Ala Arg Lys Pro Tyr Thr Ile Thr Lys
         10                  15                  20 cag cga gag cga tgg act gag gat gag cat gag agg ttt cta gaa gcc    451
```

```
Gln Arg Glu Arg Trp Thr Glu Asp Glu His Glu Arg Phe Leu Glu Ala
            25                  30                  35 ttg agg ctt tat gga aga gct tgg caa cga att gaa gaa cat att ggg      499
Leu Arg Leu Tyr Gly Arg Ala Trp Gln Arg Ile Glu Glu His Ile Gly
    40                  45                  50 aca aag act gct gtt cag atc aga agt cat gca caa aag ttc ttc aca      547
Thr Lys Thr Ala Val Gln Ile Arg Ser His Ala Gln Lys Phe Phe Thr
55                  60                  65                  70 aag ttg gag aaa gag gct gaa gtt aaa ggc atc cct gtt tgc caa gct      595
Lys Leu Glu Lys Glu Ala Glu Val Lys Gly Ile Pro Val Cys Gln Ala
                75                  80                  85 ttg gac ata gaa att ccg cct cct cgt cct aaa cga aaa ccc aat act      643
Leu Asp Ile Glu Ile Pro Pro Pro Arg Pro Lys Arg Lys Pro Asn Thr
            90                  95                  100 cct tat cct cga aaa cct ggg aac aac ggt aca tct tcc tct caa gta      691
Pro Tyr Pro Arg Lys Pro Gly Asn Asn Gly Thr Ser Ser Ser Gln Val
        105                 110                 115 tca tca gca aaa gat gca aaa ctt gtt tca tcg gcc tct tct tca cag      739
Ser Ser Ala Lys Asp Ala Lys Leu Val Ser Ser Ala Ser Ser Ser Gln
    120                 125                 130 ttg aat cag gcg ttc ttg gat ttg gaa aaa atg ccg ttc tct gag aaa      787
Leu Asn Gln Ala Phe Leu Asp Leu Glu Lys Met Pro Phe Ser Glu Lys
135                 140                 145                 150 aca tca act gga aaa gaa aat caa gat gag aat tgc tcg ggt gtt tct      835
Thr Ser Thr Gly Lys Glu Asn Gln Asp Glu Asn Cys Ser Gly Val Ser
                155                 160                 165 act gtg aac aag tat ccc tta cca acg aaa cag gta agt ggc gac att      883
Thr Val Asn Lys Tyr Pro Leu Pro Thr Lys Gln Val Ser Gly Asp Ile
            170                 175                 180 gaa aca agt aag acc tca act gtg gac aac gcg gtt caa gat gtt ccc      931
Glu Thr Ser Lys Thr Ser Thr Val Asp Asn Ala Val Gln Asp Val Pro
        185                 190                 195 aag aag aac aaa gac aaa gat ggt aac gat ggt act act gtg cac agc      979
Lys Lys Asn Lys Asp Lys Asp Gly Asn Asp Gly Thr Thr Val His Ser
    200                 205                 210 atg caa aac tac cct tgg cat ttc cac gca gat att gtg aac ggg aat     1027
Met Gln Asn Tyr Pro Trp His Phe His Ala Asp Ile Val Asn Gly Asn
215                 220                 225                 230 ata gca aaa tgc cct caa aat cat ccc tca ggt atg gta tct caa gac     1075
Ile Ala Lys Cys Pro Gln Asn His Pro Ser Gly Met Val Ser Gln Asp
                235                 240                 245 ttc atg ttt cat cct atg aga gaa gaa act cac ggg cac gca aat ctt     1123
Phe Met Phe His Pro Met Arg Glu Glu Thr His Gly His Ala Asn Leu
            250                 255                 260 caa gct aca aca gca tct gct act act aca gct tct cat caa gcg ttt     1171
Gln Ala Thr Thr Ala Ser Ala Thr Thr Thr Ala Ser His Gln Ala Phe
        265                 270                 275 cca gct tgt cat tca cag gat gat tac cgt tcg ttt ctc cag ata tca     1219
Pro Ala Cys His Ser Gln Asp Asp Tyr Arg Ser Phe Leu Gln Ile Ser
    280                 285                 290 tct act ttc tcc aat ctt att atg tca act ctc cta cag aat cct gca     1267
Ser Thr Phe Ser Asn Leu Ile Met Ser Thr Leu Leu Gln Asn Pro Ala
295                 300                 305                 310 gct cat gct gca gct aca ttc gct gct tcg gtc tgg cct tat gcg agt     1315
Ala His Ala Ala Ala Thr Phe Ala Ala Ser Val Trp Pro Tyr Ala Ser
                315                 320                 325 gtc ggg aat tct ggt gat tca tca acc cca atg agc tct tct cct cca     1363
Val Gly Asn Ser Gly Asp Ser Ser Thr Pro Met Ser Ser Ser Pro Pro
            330                 335                 340
```

```
agt ata act gcc att gcc gct gct aca gta gct gct gca act gct tgg      1411
Ser Ile Thr Ala Ile Ala Ala Ala Thr Val Ala Ala Ala Thr Ala Trp
    345             350                 355 tgg gct tct cat gga ctt ctt cct gta tgc gct cca gct cca ata aca      1459
Trp Ala Ser His Gly Leu Leu Pro Val Cys Ala Pro Ala Pro Ile Thr
360             365                 370 tgt gtt cca ttc tca act gtt gca gtt cca act cca gca atg act gaa      1507
Cys Val Pro Phe Ser Thr Val Ala Val Pro Thr Pro Ala Met Thr Glu
375             380                 385                 390 atg gat acc gtt gaa aat act caa ccg ttt gag aaa caa aac aca gct      1555
Met Asp Thr Val Glu Asn Thr Gln Pro Phe Glu Lys Gln Asn Thr Ala
                395                 400                 405 ctg caa gat caa acc ttg gct tcg aaa tct cca gct tca tca tct gat      1603
Leu Gln Asp Gln Thr Leu Ala Ser Lys Ser Pro Ala Ser Ser Ser Asp
        410                 415                 420 gat tca gat gag act gga gta acc aag cta aat gcc gac tca aaa acc      1651
Asp Ser Asp Glu Thr Gly Val Thr Lys Leu Asn Ala Asp Ser Lys Thr
            425                 430                 435 aat gat gat aaa att gag gag gtt gtt gtt act gcc gct gtg cat gac      1699
Asn Asp Asp Lys Ile Glu Glu Val Val Val Thr Ala Ala Val His Asp
440                 445                 450 tca aac act gcc cag aag aaa aat ctt gtg gac cgc tca tcg tgt ggc      1747
Ser Asn Thr Ala Gln Lys Lys Asn Leu Val Asp Arg Ser Ser Cys Gly
455             460                 465                 470 tca aat aca cct tca ggg agt gac gca gaa act gat gca tta gat aaa      1795
Ser Asn Thr Pro Ser Gly Ser Asp Ala Glu Thr Asp Ala Leu Asp Lys
                475                 480                 485 atg gag aaa gat aaa gag gat gtg aag gag aca gat gag aat cag cca      1843
Met Glu Lys Asp Lys Glu Asp Val Lys Glu Thr Asp Glu Asn Gln Pro
                490                 495                 500 gat gtt att gag tta aat aac cgt aag att aaa atg aga gac aac aac      1891
Asp Val Ile Glu Leu Asn Asn Arg Lys Ile Lys Met Arg Asp Asn Asn
        505                 510                 515 agc aac aac aat gca act act gat tcg tgg aag gaa gtc tcc gaa gag      1939
Ser Asn Asn Asn Ala Thr Thr Asp Ser Trp Lys Glu Val Ser Glu Glu
520                 525                 530 ggt cgt ata gcg ttt cag gct ctc ttt gca aga gaa aga ttg cct caa      1987
Gly Arg Ile Ala Phe Gln Ala Leu Phe Ala Arg Glu Arg Leu Pro Gln
535             540                 545                 550 agc ttt tcg cct cct caa gtg gca gag aat gtg aat aga aaa caa agt      2035
Ser Phe Ser Pro Pro Gln Val Ala Glu Asn Val Asn Arg Lys Gln Ser
                555                 560                 565 gac acg tca atg cca ttg gct cct aat ttc aaa agc cag gat tct tgt      2083
Asp Thr Ser Met Pro Leu Ala Pro Asn Phe Lys Ser Gln Asp Ser Cys
            570                 575                 580 gct gca gac caa gaa gga gta gta atg atc ggt gtt gga aca tgc aag      2131
Ala Ala Asp Gln Glu Gly Val Val Met Ile Gly Val Gly Thr Cys Lys
                585                 590                 595 agt ctt aaa acg aga cag aca gga ttt aag cca tac aag aga tgt tca      2179
Ser Leu Lys Thr Arg Gln Thr Gly Phe Lys Pro Tyr Lys Arg Cys Ser
        600                 605                 610 atg gaa gtg aaa gag agc caa gtt ggg aac ata aac aat caa agt gat      2227
Met Glu Val Lys Glu Ser Gln Val Gly Asn Ile Asn Asn Gln Ser Asp
615                 620                 625                 630 gaa aaa gtc tgc aaa agg ctt cga ttg gaa gga gaa gct tct aca tga      2275
Glu Lys Val Cys Lys Arg Leu Arg Leu Glu Gly Glu Ala Ser Thr
                635                 640                 645 cagacttgga ggtaaaaaaa aaacatccac attttatca atatctttaa atctagtgtt    2335
agtagtttgc ttctccaatc tttatgaaag agactttaa ttttccttcc gaacatttct    2395
```

```
ttggtcatgt caggttctgt accatattac cccatgtctt gtctcttgtc tctgtttgtg    2455
tatgctactt gtggtctata tgtcatctgc tactactgtt aattaaccat taagcaatgg    2515
atttgtcttt a                                                         2526
```

<210> SEQ ID NO 2
<211> LENGTH: 645
<212> TYPE: PRT
<213> ORGANISM: Arabidopsis thaliana

<400> SEQUENCE: 2

```
Met Asp Thr Asn Thr Ser Gly Glu Glu Leu Ala Lys Ala Arg Lys
 1               5                  10                  15

Pro Tyr Thr Ile Thr Lys Gln Arg Glu Arg Trp Thr Glu Asp Glu His
             20                  25                  30

Glu Arg Phe Leu Glu Ala Leu Arg Leu Tyr Gly Arg Ala Trp Gln Arg
         35                  40                  45

Ile Glu Glu His Ile Gly Thr Lys Thr Ala Val Gln Ile Arg Ser His
     50                  55                  60

Ala Gln Lys Phe Phe Thr Lys Leu Glu Lys Glu Ala Glu Val Lys Gly
 65                  70                  75                  80

Ile Pro Val Cys Gln Ala Leu Asp Ile Glu Ile Pro Pro Pro Arg Pro
                 85                  90                  95

Lys Arg Lys Pro Asn Thr Pro Tyr Pro Arg Lys Pro Gly Asn Asn Gly
            100                 105                 110

Thr Ser Ser Ser Gln Val Ser Ser Ala Lys Asp Ala Lys Leu Val Ser
        115                 120                 125

Ser Ala Ser Ser Ser Gln Leu Asn Gln Ala Phe Leu Asp Leu Glu Lys
    130                 135                 140

Met Pro Phe Ser Glu Lys Thr Ser Thr Gly Lys Glu Asn Gln Asp Glu
145                 150                 155                 160

Asn Cys Ser Gly Val Ser Thr Val Asn Lys Tyr Pro Leu Pro Thr Lys
                165                 170                 175

Gln Val Ser Gly Asp Ile Glu Thr Ser Lys Thr Ser Thr Val Asp Asn
            180                 185                 190

Ala Val Gln Asp Val Pro Lys Lys Asn Lys Asp Lys Asp Gly Asn Asp
        195                 200                 205

Gly Thr Thr Val His Ser Met Gln Asn Tyr Pro Trp His Phe His Ala
    210                 215                 220

Asp Ile Val Asn Gly Asn Ile Ala Lys Cys Pro Gln Asn His Pro Ser
225                 230                 235                 240

Gly Met Val Ser Gln Asp Phe Met Phe His Pro Met Arg Glu Glu Thr
                245                 250                 255

His Gly His Ala Asn Leu Gln Ala Thr Thr Ala Ser Ala Thr Thr Thr
            260                 265                 270

Ala Ser His Gln Ala Phe Pro Ala Cys His Ser Gln Asp Asp Tyr Arg
        275                 280                 285

Ser Phe Leu Gln Ile Ser Ser Thr Phe Ser Asn Leu Ile Met Ser Thr
    290                 295                 300

Leu Leu Gln Asn Pro Ala Ala His Ala Ala Ala Thr Phe Ala Ala Ser
305                 310                 315                 320

Val Trp Pro Tyr Ala Ser Val Gly Asn Ser Gly Asp Ser Ser Thr Pro
                325                 330                 335

Met Ser Ser Ser Pro Pro Ser Ile Thr Ala Ile Ala Ala Ala Thr Val
```

```
                    340             345             350
Ala Ala Ala Thr Ala Trp Trp Ala Ser His Gly Leu Leu Pro Val Cys
            355             360             365

Ala Pro Ala Pro Ile Thr Cys Val Pro Phe Ser Thr Val Ala Val Pro
370             375             380

Thr Pro Ala Met Thr Glu Met Asp Thr Val Glu Asn Thr Gln Pro Phe
385             390             395             400

Glu Lys Gln Asn Thr Ala Leu Gln Asp Gln Thr Leu Ala Ser Lys Ser
            405             410             415

Pro Ala Ser Ser Asp Asp Ser Asp Glu Thr Gly Val Thr Lys Leu
            420             425             430

Asn Ala Asp Ser Lys Thr Asn Asp Lys Ile Glu Glu Val Val Val
            435             440             445

Thr Ala Ala Val His Asp Ser Asn Thr Ala Gln Lys Lys Asn Leu Val
            450             455             460

Asp Arg Ser Ser Cys Gly Ser Asn Thr Pro Ser Gly Ser Asp Ala Glu
465             470             475             480

Thr Asp Ala Leu Asp Lys Met Glu Lys Asp Lys Glu Asp Val Lys Glu
            485             490             495

Thr Asp Glu Asn Gln Pro Asp Val Ile Glu Leu Asn Asn Arg Lys Ile
            500             505             510

Lys Met Arg Asp Asn Asn Ser Asn Asn Asn Ala Thr Thr Asp Ser Trp
            515             520             525

Lys Glu Val Ser Glu Glu Gly Arg Ile Ala Phe Gln Ala Leu Phe Ala
            530             535             540

Arg Glu Arg Leu Pro Gln Ser Phe Ser Pro Pro Gln Val Ala Glu Asn
545             550             555             560

Val Asn Arg Lys Gln Ser Asp Thr Ser Met Pro Leu Ala Pro Asn Phe
            565             570             575

Lys Ser Gln Asp Ser Cys Ala Ala Asp Gln Glu Gly Val Val Met Ile
            580             585             590

Gly Val Gly Thr Cys Lys Ser Leu Lys Thr Arg Gln Thr Gly Phe Lys
            595             600             605

Pro Tyr Lys Arg Cys Ser Met Glu Val Lys Glu Ser Gln Val Gly Asn
            610             615             620

Ile Asn Asn Gln Ser Asp Glu Lys Val Cys Lys Arg Leu Arg Leu Glu
625             630             635             640

Gly Glu Ala Ser Thr
            645

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 3
atggatacta atacatct                                                    18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 4
ctagatttaa agatatta                                                     18

<210> SEQ ID NO 5
<211> LENGTH: 125
<212> TYPE: DNA
<213> ORGANISM: Artificial Sequence
<220> FEATURE:
<223> OTHER INFORMATION: Description of Artificial Sequence: Mutant

<400> SEQUENCE: 5
cgttaccgac cgttttcatc cctatactca aaagagtaac cagtacgttt gattcgtctt        60
gatggaactc aaagctaagt attttcaaat tacattgtgg atgatccaga tgtgagcaag       120
tgatt                                                                  125

<210> SEQ ID NO 6
<211> LENGTH: 666
<212> TYPE: DNA
<213> ORGANISM: Artificial Sequence
<220> FEATURE:
<223> OTHER INFORMATION: Description of Artificial Sequence: Mutant

<400> SEQUENCE: 6
atcctacttt catccctgct aaagaggtta tcacaacggc tttgcaattt gaaaactttc        60
atgtttgggg agatcaaaga tggtttcttt tttatacttt acttgttaga gaggatttga       120
agcagcgaat agctgcaccg gtcctgttat ggatactaat acatctggag aagaattatt       180
agctaaggta ctactactaa tgaaataaga ttggtgtttt tttgtttgag agatttggac       240
tgttgttgtg tgaagatttg attttctttt gggttttcaa atgtttaggc aagaaagcca       300
tatacaataa caaagcagcg agrgcgatgg actgaggatg agcatgagag gtttctagaa       360
gccttgaggc tttatggaag agcttggcaa cgaattgaag gtcgraaggt ttatcttttg       420
aatgtttagt ttgaactctt tgagatttta tattcctttg tttaggagtg tctttatctc       480
ctcttgattg ggagattcct tcttttcttt tcatttttgtg tgcagaacat attgggacaa       540
agactgctgt tcagatcaga agtcatgcac aaaagttctt cacaaaggta agttgatgat       600
cctttcagat cccggtgaaa cggtcgggaa actagctcta ccgtttccgt ttccgtttac       660
cgtttt                                                                 666

<210> SEQ ID NO 7
<211> LENGTH: 55
<212> TYPE: PRT
<213> ORGANISM: Arabidopsis thaliana

<400> SEQUENCE: 7

Thr Ile Thr Lys Gln Arg Glu Arg Trp Thr Glu Asp Glu His Glu Arg
  1               5                  10                  15

Phe Leu Glu Ala Leu Arg Leu Tyr Gly Arg Ala Trp Gln Arg Ile Glu
                 20                  25                  30

Glu His Ile Gly Thr Lys Thr Ala Val Gln Ile Arg Ser His Ala Gln
             35                  40                  45

Lys Phe Phe Thr Lys Leu Glu
         50                  55

<210> SEQ ID NO 8
<211> LENGTH: 16
<212> TYPE: PRT
<213> ORGANISM: Unknown Organism
```

```
<220> FEATURE:
<223> OTHER INFORMATION: Description of Unknown Organism: TEA domain of
      TEC1 (Swissprot database)

<400> SEQUENCE: 8

Trp Ser Glu Lys Val Glu Glu Ala Phe Leu Glu Ala Leu Arg Leu Ile
 1               5                  10                  15

<210> SEQ ID NO 9
<211> LENGTH: 16
<212> TYPE: PRT
<213> ORGANISM: Unknown Organism
<220> FEATURE:
<223> OTHER INFORMATION: Description of Unknown Organism: TEA domain of
      TEF1 (Swissprot database)

<400> SEQUENCE: 9

Trp Ser Pro Asp Ile Glu Gln Ser Phe Gln Glu Ala Leu Ala Ile Tyr
 1               5                  10                  15

<210> SEQ ID NO 10
<211> LENGTH: 41
<212> TYPE: PRT
<213> ORGANISM: Unknown Organism
<220> FEATURE:
<223> OTHER INFORMATION: Description of Unknown Organism: Accesion no.
      P25357

<400> SEQUENCE: 10

Trp Ser Val Arg Glu Ser Gln Leu Phe Pro Glu Leu Leu Lys Glu Phe
 1               5                  10                  15

Gly Ser Gln Trp Ser Leu Ile Ser Glu Lys Leu Gly Thr Lys Ser Thr
            20                  25                  30

Thr Asn Val Arg Asn Tyr Tyr Gln Arg
        35                  40

<210> SEQ ID NO 11
<211> LENGTH: 47
<212> TYPE: PRT
<213> ORGANISM: Unknown Organism
<220> FEATURE:
<223> OTHER INFORMATION: Description of Unknown Organism: BAS1 R1
      (Swissprot Accession no. P22035)

<400> SEQUENCE: 11

Trp Thr Gln Glu Glu Asp Glu Gln Leu Leu Lys Ala Tyr Glu Glu His
 1               5                  10                  15

Gly Pro His Trp Leu Ser Ile Ser Met Asp Ile Pro Gly Arg Thr Glu
            20                  25                  30

Asp Gln Cys Ala Lys Arg Tyr Ile Glu Val Leu Gly Pro Gly Ser
        35                  40                  45

<210> SEQ ID NO 12
<211> LENGTH: 47
<212> TYPE: PRT
<213> ORGANISM: Unknown Organism
<220> FEATURE:
<223> OTHER INFORMATION: Description of Unknown Organism: BAS1 R2
      (Swissprot Accession no. P22035)

<400> SEQUENCE: 12

Trp Thr Leu Glu Glu Asp Leu Asn Leu Ile Ser Lys Val Lys Ala Tyr
 1               5                  10                  15

Gly Thr Lys Trp Arg Lys Ile Ser Ser Glu Met Glu Phe Arg Pro Ser
            20                  25                  30
```

```
Leu Thr Cys Arg Asn Arg Trp Arg Lys Ile Ile Thr Met Val Val
        35                  40                  45
```

<210> SEQ ID NO 13
<211> LENGTH: 57
<212> TYPE: PRT
<213> ORGANISM: Arabidopsis thaliana

<400> SEQUENCE: 13

```
Thr Ile Thr Lys Gln Arg Glu Arg Trp Thr Glu Asp Glu His Glu Arg
  1               5                  10                  15

Phe Leu Glu Ala Leu Arg Leu Tyr Gly Arg Ala Trp Gln Arg Ile Glu
             20                  25                  30

Glu His Ile Gly Thr Lys Thr Ala Val Gln Ile Arg Ser His Ala Gln
        35                  40                  45

Lys Phe Phe Thr Lys Leu Glu Lys Ala
        50                  55
```

<210> SEQ ID NO 14
<211> LENGTH: 83
<212> TYPE: PRT
<213> ORGANISM: Arabidopsis thaliana

<400> SEQUENCE: 14

```
Met Asp Thr Asn Thr Ser Gly Glu Glu Leu Leu Ala Lys Ala Arg Lys
  1               5                  10                  15

Pro Tyr Thr Ile Thr Lys Gln Arg Glu Arg Trp Thr Glu Asp Glu His
             20                  25                  30

Glu Arg Phe Leu Glu Ala Leu Arg Leu Tyr Gly Arg Ala Trp Gln Arg
        35                  40                  45

Ile Glu Glu His Ile Gly Thr Lys Thr Ala Val Gln Ile Arg Ser His
     50                  55                  60

Ala Gln Lys Phe Phe Thr Lys Leu Glu Lys Glu Ala Glu Val Lys Gly
 65                  70                  75                  80

Ile Pro Val
```

<210> SEQ ID NO 15
<211> LENGTH: 111
<212> TYPE: PRT
<213> ORGANISM: Arabidopsis thaliana

<400> SEQUENCE: 15

```
Gly Arg Ile Ala Phe Gln Ala Leu Phe Ala Arg Glu Arg Leu Pro Gln
  1               5                  10                  15

Ser Phe Ser Pro Pro Gln Val Ala Glu Asn Val Asn Arg Lys Gln Ser
             20                  25                  30

Asp Thr Ser Met Pro Leu Ala Pro Asn Phe Lys Ser Gln Asp Ser Cys
        35                  40                  45

Ala Ala Asp Gln Glu Gly Val Val Met Ile Gly Val Gly Thr Cys Lys
     50                  55                  60

Ser Leu Lys Thr Arg Gln Thr Gly Phe Lys Pro Tyr Lys Arg Cys Ser
 65                  70                  75                  80

Met Glu Val Lys Glu Ser Gln Val Gly Asn Ile Asn Asn Gln Ser Asp
             85                  90                  95

Glu Lys Val Cys Lys Arg Leu Arg Leu Glu Gly Glu Ala Ser Thr
        100                 105                 110
```

```
<210> SEQ ID NO 16
<211> LENGTH: 83
<212> TYPE: PRT
<213> ORGANISM: Arabidopsis thaliana

<400> SEQUENCE: 16

Ile Ala Thr Thr Glu Ala Gly Glu Ala Pro Glu Lys Lys Val Arg Lys
  1               5                  10                  15

Ala Tyr Thr Ile Thr Lys Ser Arg Glu Ser Trp Thr Glu Gly Glu His
             20                  25                  30

Asp Lys Phe Leu Glu Ala Leu Gln Leu Phe Asp Arg Asp Trp Lys Lys
         35                  40                  45

Ile Glu Asp Phe Phe Gly Ser Lys Thr Val Ile Gln Ile Arg Ser His
     50                  55                  60

Ala Gln Lys Tyr Phe Leu Lys Val Gln Lys Asn Gly Thr Leu Ala His
 65                  70                  75                  80

Ile Pro Thr

<210> SEQ ID NO 17
<211> LENGTH: 118
<212> TYPE: PRT
<213> ORGANISM: Oryza sativa

<400> SEQUENCE: 17

Phe Asp Ala Leu Phe Ser Arg Glu Arg Leu Pro Gln Ser Phe Ser Pro
  1               5                  10                  15

Pro Gln Val Glu Gly Ser Lys Glu Ile Ser Lys Glu Glu Asp Glu
             20                  25                  30

Val Thr Thr Val Thr Val Asp Leu Asn Lys Asn Ala Ala Ile Ile Asp
             35                  40                  45

Gln Glu Leu Asp Thr Ala Asp Glu Pro Arg Ala Ser Phe Pro Asn Glu
     50                  55                  60

Leu Ser Asn Leu Lys Leu Lys Ser Arg Arg Thr Gly Phe Lys Pro Tyr
 65                  70                  75                  80

Lys Arg Cys Ser Val Glu Ala Lys Glu Asn Arg Val Pro Ala Ser Asp
                 85                  90                  95

Glu Val Gly Thr Lys Arg Ile Arg Leu Glu Ser Glu Asp Arg His Asp
            100                 105                 110

Leu Leu Ser Thr Trp Val
            115

<210> SEQ ID NO 18
<211> LENGTH: 1738
<212> TYPE: DNA
<213> ORGANISM: Arabidopsis thaliana

<400> SEQUENCE: 18
caaacatcaa cgtagggatc cgtgaaatat ttaaatccgg tttgtttggt tattttggaa      60
taatttcggt tatttcaatt agattcgggt agttcagttc ttcggttagt aacaaaaact     120
ggtctattgt tttttggtta acctagaacc gaaccgaact aaccaaagtt ctcggtaacc     180
ttttgtagtg gcttcctgac cgatgaggcc gtcaacttca aaaaatattg caactaagct     240
ctgctccaaa attagagtat ctataactat gttaaacgct tctgctttaa gcaaaacaca     300
gttgtaagct ggaatctaaa aaaatgagtg taatgatgtt tgctgaattc cataaataaa     360
tactacatgc ttcggttaag acttaagagt aattaatgtt ccttaatttc tacaaatgtt     420
atataagcaa gttgaccaaa gttctcgatg ataatttgtt gaaattttgt ataggcattg     480
```

-continued

```
catgatatta tatgaaaaga tgaagatttt tatacagacg caagttcccc gagcagtcca      540
agcttgtcgg gtttaattca actatgttaa tacgcaaatt tatatagaat aggcgtaaaa      600
gtgaggccca tacaatgtct tattacaagc ccagatccag catagccaat acgtagcagt      660
acaccatcac agctggcacc gtacccactt gtttagtcgt ccaagtttgt accaataatc      720
gtttacacgt aagcaattgt ggaccaccac actcactttt acctacgtga gcttcacatt      780
gaagcttctg gctcgtagag aagcaacttg agatatacca aaaagtgcag tagacagcca      840
ctacaatatc accacgtgtc gatctgcgat gacttctgtt tttccattta tacccttggt      900
gctgttccag cctcaaataa cttttcaatt aaaattttc caaaaattag gggcaaaaat       960
tgttgtggct gagattgctt ctggcttctc ttcttcttct tccagtcttc ttcagcctaa     1020
aacagtcttc cttcttcttc ttcttcttct tcttctttca gttatcttct tccttcttct     1080
ctctgttttt taaatttatt tttagagatt ttttttttgtt ttgcttccga tttgattatt    1140
tccgggaacg atgacttctc cggggagttc ccggtgagat gataagtcag attgcatact     1200
tgtctcctcc atggctactc tcaagggtat aacagtttac attatgagca gtttctagga    1260
ttcctataac atactaagat ctctgtttgg ctgctgagaa acttatacaa gcgcattaac    1320
taaatcttat tagctctaaa agttagcata aatgatacga atctggtgat tgattactga    1380
tatgaagatt tgtgaaggtt ttggctgagg tggattcgtt tgggtgaggc ttttgtgaat    1440
aataataaag ggaattcttt tgagttctgc tggagaagca gcgactgttt cacggtggtc    1500
tttgaaaaga tttctctttt gaatttcgct catcactctt atcttagtgt ttgtggataa    1560
atatttctca taaagtactt tctcctttgc agtttctcta gaatctaaag aggttatcac    1620
aacggctttg caatttgaaa actttcatgt ttggggagat caaagatggt ttcttttta     1680 tactttactt gttagagagg atttgaagca gcgaatagct gcaaccggtc ctgttatg     1738
```

<210> SEQ ID NO 19
<211> LENGTH: 447
<212> TYPE: DNA
<213> ORGANISM: Unknown Organism
<220> FEATURE:
<223> OTHER INFORMATION: Description of Unknown Organism: Nucleotide
      sequence of EST 162I3T7, Accession no. R30439
<220> FEATURE:
<221> NAME/KEY: misc_feature
<222> LOCATION: (37, 204, 275, 335, 347, 353, 363, 367)
<223> OTHER INFORMATION: n is a, g, c, or t
<220> FEATURE:
<221> NAME/KEY: misc_feature
<222> LOCATION: (377, 384, 392, 393, 419, 428, 429, 436, 439)
<223> OTHER INFORMATION: n is a, g, c, or t

<400> SEQUENCE: 19

```
ctagacgatc tctatcttga ataaaatacc gataatnacc tcaaccaatc cggtggtcgc       60
cgaagtaata ccggcggaaa cttctacaga tgctacagag acgacgattg caacgacgga      120
agctggtgaa gcaccggaga agaaggtgag gaaagcttac acaatcacca agtctagaga      180
gagttggact gaaggagaac acgncaagtt tctggaagct cttcaattgt ttgatcgtga      240
ctggaaaaag atagaagatt ttttggttc aaagncagtt attcagatca ggagccatgc      300
ccagaaatac tttctaaagg tccaaaaaaa tgggncttta gcacatnttc ccnccccta      360 ggnctanggg caaagtngct catncatatc cnnaaaaggc attcgaaaaa ttgctcaant    420
ttcggttnnc gtttcnatng cctttcc                                        447
```

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 20
gatataccgg taacgaaaac gaacgg                                    26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 21
ttcgtttccg tcccgcaagt taaata                                    26

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 22
cgttaccgac cgtttttcat cccta                                     25

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 23
acgaacggga taaatacggt aatc                                      24

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 24
gttagtttta tcccgatcga tttcga                                    26

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 25
accgctttga ttgagaagct g                                         21

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Primer

```
<400> SEQUENCE: 26
catcaacgta gggatccgtg aaatat                                              26

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 27
ggactagtaa caggaccggt tgcagctatt c                                        31
```